(12) United States Patent
McCarthy et al.

(10) Patent No.: US 10,321,961 B2
(45) Date of Patent: Jun. 18, 2019

(54) PATIENT SPECIFIC IMPLANTATION METHOD FOR RANGE OF MOTION HIP IMPINGEMENT

(71) Applicant: Howmedica Osteonics Corp., Mahwah, NJ (US)

(72) Inventors: Thomas Francis McCarthy, Neshanic Station, NJ (US); Vincent Alipit, Nanuet, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 253 days.

(21) Appl. No.: 15/330,882

(22) Filed: Nov. 7, 2016

(65) Prior Publication Data
US 2017/0128135 A1    May 11, 2017

Related U.S. Application Data

(60) Provisional application No. 62/251,441, filed on Nov. 5, 2015.

(51) Int. Cl.
*A61B 34/10* (2016.01)
*A61F 2/46* (2006.01)
(Continued)

(52) U.S. Cl.
CPC ............ *A61B 34/10* (2016.02); *A61B 5/1121* (2013.01); *A61B 6/505* (2013.01);
(Continued)

(58) Field of Classification Search
CPC .... A61F 2/46; A61F 2/34; A61F 2/468; A61F 2/3662; A61B 34/10; A61B 6/505
See application file for complete search history.

(56) References Cited

U.S. PATENT DOCUMENTS 5,037,424 A    8/1991 Aboczsky
5,571,111 A    11/1996 Aboczky
(Continued)

FOREIGN PATENT DOCUMENTS

EP    1994914 B1    5/2012

OTHER PUBLICATIONS

Berthonnaud et al., "Accessing 3D Location of Standing Pelvis: Relative Position of Sacral Plateau and Acetabular Cavities versus Pelvis," Radiology Research and Practice, vol. 2012, 10 pages, Jan. 2012.

(Continued)

*Primary Examiner* — Christopher J Beccia
(74) *Attorney, Agent, or Firm* — Lerner, David, Littenberg, Krumholz & Mentlik, LLP

(57) ABSTRACT

A method for avoiding impingement between an implanted prosthetic hip stem and acetabular cup uses at least one digital x-ray of a standing patient preferably including a lateral x-ray to determine a pelvic tilt angle of the patient. A hip stem is virtually implanted at an initial stem version angle into a virtual femur constructed from the digital x-ray. Data of at least one hip joint motion is obtained from at least one individual. A range of inclination and anteversion angles is calculated for a virtually implanted acetabular cup that avoids impingement with the virtually implanted hip stem. The calculated range of inclination or anteversion angles is based at least in part on the pelvic tilt angle of the patient, the initial hip stem version angle and the obtained joint motion data.

15 Claims, 28 Drawing Sheets

(51) Int. Cl.
*A61B 5/11* (2006.01)
*A61B 6/00* (2006.01)

(52) U.S. Cl.
CPC . *A61B 2034/104* (2016.02); *A61F 2002/4633* (2013.01); *A61F 2002/4668* (2013.01)

(56) References Cited

U.S. PATENT DOCUMENTS

| | | | |
|---|---|---|---|
| 6,205,411 B1 * | 3/2001 | DiGioia, III | G06F 19/00 703/11 |
| 6,395,005 B1 | 5/2002 | Lovell | |
| 6,405,072 B1 | 6/2002 | Cosman | |
| 6,428,547 B1 | 8/2002 | Vilsmeier et al. | |
| 6,701,174 B1 | 3/2004 | Krause et al. | |
| 6,990,368 B2 | 1/2006 | Simon et al. | |
| 7,039,225 B2 | 5/2006 | Tanaka et al. | |
| 7,194,295 B2 | 3/2007 | Vilsmeier | |
| 7,699,793 B2 | 4/2010 | Gotte et al. | |
| 7,837,621 B2 | 11/2010 | Krause et al. | |
| 7,877,131 B2 | 1/2011 | Jansen et al. | |
| 8,078,254 B2 | 12/2011 | Murphy | |
| 8,170,641 B2 | 5/2012 | Belcher | |
| 8,206,405 B2 | 6/2012 | Beverland et al. | |
| 8,394,036 B2 | 3/2013 | Kozak | |
| 8,449,551 B2 | 5/2013 | Amiot et al. | |
| 8,932,299 B2 | 1/2015 | Bono et al. | |
| 2002/0077540 A1 | 6/2002 | Kienzle | |
| 2004/0087852 A1 | 5/2004 | Chen et al. | |
| 2005/0065617 A1 | 3/2005 | Moctezuma de la Barrera et al. | |
| 2006/0264731 A1 * | 11/2006 | Murphy | A61F 2/4657 600/407 |
| 2008/0033442 A1 | 2/2008 | Amiot et al. | |
| 2010/0152859 A1 | 6/2010 | Thompson et al. | |
| 2011/0313424 A1 | 12/2011 | Bono et al. | |
| 2012/0172884 A1 | 7/2012 | Zheng et al. | |
| 2013/0304429 A1 * | 11/2013 | Haimerl | A61B 34/10 703/1 |
| 2014/0277555 A1 * | 9/2014 | Meridew | A61B 90/37 623/22.12 |
| 2015/0088145 A1 | 3/2015 | McCarthy | |

OTHER PUBLICATIONS

Egglie et al., Value of preoperative planning in total hip arthroplasty, Journal of Bone and Joint Surgery, vol. 80-B, No. 3, May 1998.

Miller, EOS Imaging System is an Emerging New Technology, www.bioclinica.com, 1 page, Dec. 5, 2012.

Murray, The definition and measurement of acetabular orientation, J Bone Joint Surg Br., 75(B):228-32, Mar. 1993.

Lazennec et al., Pelvis and total hip arthroplasty acetabular component orientations in sitting and standing positions: measurements reproductibility with EOS imaging system versus conventional radiographies, Orthop Traumatol Surg Res., 97(4):373-80, May 12, 2011, abstract.

Babisch et. al. The Rationale for Tilt-Adjusted Acetabular Cup Navigation.The Journal of Bone and Joint Surgery (Impact Factor: 3.23). Feb. 2008; 90(2):357-65.

Lewinnek et al., "Dislocations After Total Hip-Replacement Arthroplasties," The Journal of Bone and Joint Surgery, vol. 60-A, No. 2, Mar. 1978, pp. 217-220.

Callanan et al., "Risk Factors for Cup Malpositioning," Clinical Orthopaedics and Related Research, vol. 469, No. 2, pp. 319-329, Feb. 2011.

* cited by examiner

| | |
|---|---|
| IMPLANT GEOMETRY HEAD SIZE | 28mm, 32mm, 36mm, MDM |
| IMPLANT GEOMETRY STEM NECK ANGLE | 127° AND 132° |
| PELVIC TILT | 0° TO 28° (Au) |
| STEM VERSION | 5° – 15° – 25° |
| MOTION | SQUAT, CHAIR RISE, PICKUP, TURN (PIVOT), TOILET, WALK, STAIR-UP, STAIR-DOWN |
| CUP INCLINATION | |
| CUP VERSION | |

FIG. 14

Figure 22 shows a safe zone for a size 7 hip stem (Accolade Stryker Corp) with 0° pelvic tilt and a stem version of 15° for subject 1.

Figure 23 shows a safe zone for a 5° forward pelvic tilt in standing x-ray and 5° backward pelvic tilt on OR table and stem version of 10° for subject 1.

Figure 24 shows a safe zone for a 5° backward pelvic tilt when standing x-ray is 5° forward pelvic tilt on OR table with 10° stem version for subject 1.

Figure 25 shows a safe zone for 0° pelvic tilt and a stem in 15° version for subject 1.

FIGURE 26 IS A STANDING LATERAL X-RAY SHOWING PELVIC TILT.

PATIENT SPECIFIC IMPLANTATION METHOD FOR RANGE OF MOTION HIP IMPINGEMENT

CROSS-REFERENCE TO RELATED APPLICATIONS

This application claims the benefit of the filing date of U.S. Provisional Patent Application No. 62/251,441 filed Nov. 5, 2015, the disclosure of which is hereby incorporated herein by reference.

BACKGROUND OF THE INVENTION

This invention relates to a method for avoiding impingement between an acetabular cup and a femoral component; a femoral component and bone; or bone and bone.

Hip surgery requires the implantation of a femoral stem and an acetabular cup. The femoral stem has a spherical head that attaches to the neck of the stem and is free to articulate within a bearing insert that is fitted into the shell of an acetabular cup. Should the stem and cup not be positioned/aligned accurately, the neck of the stem may impinge on the lip of the insert resulting in a levering action that could allow the femoral head to cam out of the insert resulting in a permanent dislocation of the head. The impingement can also lead to excessive component wear and possibly failure.

In addition, a malpositioned cup can result in excessive liner wear even without impingement. A shell with a high abduction (inclination) angle can have joint forces concentrated near the cup liner rim, thereby increasing the wear rate due to concentrated forces.

A person's pelvis and two femurs form a "matched set" allowing the person to articulate one with the other under normal motions such as walking, squatting, etc., without dislocation. This matched set is different in every individual. One person may have a natural pelvic position such that it is flexed forward when standing. Another may have a pelvis that is flexed backward when standing. The amount of pelvic flexion is also referred to as pelvic tilt. Likewise, the amount of femoral neck version that matches with the pelvis will be different for each individual.

Stem/cup impingement can serve as a fulcrum that could lever the femoral head out of the cup, which is called dislocation, a serious clinical issue. Orthopaedic surgeons attempt to place an acetabular cup in the pelvis in an orientation that will hopefully not result in a stem/cup impingement. In placing the cup, it would help if the surgeons knew what the natural pelvic tilt and stem version were, therefore they could try to recreate it. However, this data, for the most part, is not currently available to the surgeon to take into consideration.

Reducing or eliminating the chance for neck/insert impingement and high inclination angles is critical to eliminating dislocation and wear, which can ultimately result in a revision surgery to correct compound alignment (abduction and anteversion).

The method of the present invention allows the surgeon to choose motions that matter (e.g. squatting for Asian population or gardeners). The surgeon can decide on implant types based on motions (e.g. a large femoral head vs. a smaller head, a femoral stem with different neck versions . . . ). The surgeon will know the boundaries of adjusting cup position, which is important to balance need to avoid iliopsoas tendon impingement with cup rim and high-wear inclination angles.

A study by H. Malchau et al., Clin. Orthop. Relat. Res. (2011) 469; 319-329 reviewed the implanted acetabular cup position post implantation in relation to the pelvic anatomy. The study of 1823 patients revealed that the cup position varied widely in reference to their described target zone.

One main reason for such variation is that the exact position of the patient's pelvis is not known in relation to the operating room (OR) table. Surgeons must rely on their experience to know how to position the cup, however the cup may not be implanted in the intended orientation. This is especially true with respect to less experienced surgeons.

Alignment of an acetabular cup can be achieved with an alignment guide that attaches to an insertion rod for facilitating the insertion of the acetabular cup into the acetabulum. The alignment guide preferably references the surgical table on which the patient rests. Conventionally, it is assumed that the patient's pelvis is parallel to the table, and that the surgical table is parallel to the floor. Based on such assumptions, the ordinary position (in most patients) for the acetabular cup is 45° of inclination (abduction) and 20° of anteversion. For a discussion of angles of anteversion and also inclination or abduction of the acetabular cup when installed in the acetabulum, see, for example, U.S. Pat. No. 6,395,005, the disclosure of which is incorporated by reference herein in its entirety.

It has been found based on post-operative x-rays, however, that despite the alignment guide being parallel to the floor during insertion, of the acetabular cup, the resultant inclination or anteversion of the acetabulum in relation to the alignment guide is often different than expected and, thus, the acetabular cup has been installed at a less than ideal position. The pelvic position changes in relation to the operating room table which is not recognized during the procedure for example.

Presently most orthopedic companies offer instrumentation to direct reaming for acetabular cups and cup impaction which is an antenna-like device that attaches to either the reamer shaft or the cup impaction tool. Such cup alignment instruments are shown in, for example, U.S. Pat. Nos. 5,037,424, 5,571,111 and 6,395,005. When an x-shaped "antenna" is used a cup impactor that is oriented 45 degrees to the floor and 20 degrees to the long axis of the patient. The 'X' shape on the antenna is set parallel to the floor, and one leg of the 'X' set in line with the long axis of the body. One leg is for a left leg operation, and the other for a right leg operation. Manual hip acetabular cup placement instruments use the operating table or floor as a reference with the assumption that pelvic tilt does not matter. Almost all surgeons place the acetabular cup in first and the stem second, therefore not taking into account the stem version which cannot be adjusted to the cup position.

Some of the drawbacks of this type of instrument are that the pelvis usually shifts when the patient is laid on the operating room table. If the pelvis does not shift, and the surgeon wants a 45/20 cup position, then the surgeon could use the instrument as is and get the perfect 45/20 alignment within the bone. However, most times the pelvis does shift in three possible planes: tilt, obliquity, and rotation. The surgeon does not know in which direction or by how much and therefore must use his experience or intuition to apply a correction factor to the direction of cup impaction. The actual cup orientation after impaction is not usually known until after the operation is complete and a post-operative x-ray is taken, and the patient is in recovery, and therefore at a time when changes to cup orientation are not possible without reoperation.

Another drawback is that the current antenna/impactor combination is set at set angles. For example a 45/20 degree abduction/anteversion orientation. If the surgeon determines that orientation of 40° to the floor and 15° to the long axis of the patient's femur is best for the patient, the set angles are of little use, or again the surgeon has to estimate a correct alignment. The orientation of the antenna/impactor combination in practice is set visually. The antenna shaft is set vertically, with the antenna 'X' cross bars parallel to the floor. The 20 degree orientation to the patient long axis is visual as well. Many surgeons do not use the antenna at all.

Some major prosthetic hip joint companies offer a navigation option to surgeons. This system uses cameras in the operating room and optical trackers on instrumentation. From a clinical perspective, the major drawbacks for navigation are that the technique involves placing invasive pins having the tracker thereon in the patient pelvis and femur. The pins are placed in the pelvis and the femur, through the skin and screwed into the bone. Using pins results in multiple separate wounds and increases the possibility of infection. This technique is also time intensive. Pins must be placed and pointers with trackers on them are used multiple times to register anatomy. This technique has a learning curve. The software and technique require extensive training and practical experience. Some systems require a pre-op CT scan which is costly. Navigation systems assume that the pelvis is in the same orientation for all cases.

A more recent development is digital imaging which produces an x-ray like image on a digital receiver. Once digitized, the digital image can be used to identify points in order for the system to calculate lengths and angles which could be used by the surgeon to help to identify how the pelvis is oriented to the operating room table. The surgeon can take pre-operative and intra-operative x-rays and pick points on the screen to calculate lengths and angles. This is a relatively new technology with a relatively small amount of users.

The digital x-rays can be visually observed for comparison. The system can aid the user by allowing the user to plan by designating the desired cup inclination and version angles pre-operatively as well as taking dimensions that will help to designate leg length and femoral stem offset corrections. Taking dimensions that will measure the cup inclination and version angles of the actual implanted cup intra-operatively as well as taking dimensions that show that actual leg length and offset of the trials or implants.

These current digital imaging systems do not have an algorithm that tries to compare pre-operative and intra-operative images to calculate how the intra-operative pelvic position changes in orientation to a pre-operative image. Furthermore, the current digital systems don't calculate the cup impaction angles that would account for these changes. Instead the cup needs to be first impacted into the bone prior to taking the image, and reoriented if not in the desired position. Reorienting the shell could compromise the fit and security of the cup to the acetabular bone cavity. Multiple reorientations could possibly compromise the fit to the point that a secure fit is no longer achieved. In this situation, the surgeon may have to remove the shell, ream up to the next size shell, and start over. The removal of further acetabular bone is not ideal as this could compromise the overall strength of the remaining bone, and reduce the amount of bone for any future revisions. Current digital imaging techniques require successive intra-operative images, exposing the patient and the surgical team to higher levels of radiation than with a single image.

U.S. Publication No. 2015/0088145, the disclosure of which is incorporated herein in its entirety, uses a combination of digital imaging and orientation technology to improve upon the limitations described above, along with an algorithm that determines the amount of pelvic movement in the three planes (obliquity, tilt, rotation) that is used as input for the orientation technology. U.S. Publication 2015/0088145 calculates pelvic tilt obliquity and rotation intra-operatively which no other system does. Most pre-operative x-ray images are taken lying down, and hence placing the pelvis in an unnatural position. A standing x-ray is the gold standard as the amount of pelvic tilt when standing is what is right for that individual. This invention serves to recreate the natural standing x-ray tilt and, if desired, obliquity and rotation amount intra-operatively by adjusting the orientation of reaming and cup impaction, and performing these functions at the pre-op plan angles determined by the user (e.g. at 40° inclination and 15° anteversion).

U.S. Publication No. 2015/088145 uses a method for aligning an acetabular cup including: taking a pre-operative preferably standing anterior/posterior view digital x-ray image and a lateral view standing digital x-ray image of the pelvis of a patient. A desired cup abduction and anteversion angle is determined based on two standing x-ray images. At least three points on the digital anterior/posterior digital x-ray image and at least two points on the lateral digital x-ray image are identified. The lengths and angles between each of the points on both the anterior/posterior digital image and the lateral digital image are calculated. A patient is positioned on an operating table in an operating room. The preferred operating table has a reference element thereon. In the preferred embodiment, the operating room has a navigation system therein, the preferred operating table has a navigation tracker mounted in a known position with respect to the operating table. Alternately, the reference system could reference the floor or other fixed point including the operating room table. At least one pelvic digital x-ray image of the patient positioned on the operating table is taken with the x-rays including the reference element. At least three points are identified on the intra-operative x-ray image. In the preferred embodiment, the points corresponding to the points on the pre-operative x-ray image. The lengths and angles between each of the at least three points on the intra-operative digital images are then calculated. An intra-operative angular deviation of the acetabular cup insertion instrument from the desired abduction and anteversion angle i.e. calculated by comparing the dimensional differences between the points on the pre-operative standing x-ray images and the at least one intra-operative x-ray image. The insertion instrument is then aligned to a calculated angular position, based on the intra-operative deviation, using the navigation camera and a navigation tracker mounted on the insertion instrument.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF SUMMARY OF THE INVENTION

The present invention relates to a surgical technique or method to define an area for cup placement to avoid component to component impingement, component to bone impingement, or bone to bone impingement taking into account pelvic tilt, stem position within the femur including stem neck version, cup inclination and anteversion, component geometry and actual hip joint motion data.

The method avoids impingement between an implanted prosthetic hip stem (femoral component) and acetabular cup. Initially, a digital, preferably lateral, x-ray of a standing patient is obtained. Then a pelvic tilt angle of the patient is determined from the standing x-ray. A hip stem is virtually implanted at an initial stem version angle into a virtual femur using femur data from the digital x-ray. Digitized hip joint motion data is obtained from at least one individual and cup inclination and version are calculated using the digitized x-ray data and motion data. A range of inclination and anteversion angles for a virtually implanted acetabular cup that avoids impingement with the virtually implanted hip stem are calculated. The calculated range of inclination and anteversion angles is based at least in part on the pelvic tilt angle of the patient, the initial hip stem version angle and the obtained digitized joint motion data.

Preferably, the hip motion data is selected the group consisting of pivoting on one foot, squatting, sitting in a chair, rising from a chair, picking up an object, climbing up stairs, climbing down stairs, rising from a toilet and walking. Of course, other human motions can be used to provide digital data for use by the software. The virtually implanted acetabular cup is virtually implanted at multiple inclination angles and multiple anteversion angles, and the virtual hip implant is moved through a range of motion based on the pelvic tilt and motion data. The digitized hip joint motion data is preferably obtained from external motion detecting elements mounted on the at least one individual such as shown in publication. Preferably, the virtual hip stem and virtual acetabular cup are digitized versions selected from a group of commercially available hip stems and acetabular cups.

A safe zone is calculated when calculating the range of inclination and anteversion angles for the virtually implanted acetabular cup, the safe zone being where impingement with the virtually implanted hip stem at an initial pre-selected stem version angle is avoided throughout a range of hip joint motion of the at least one daily activity.

The method for avoiding impingement between an implanted prosthetic hip stem (femoral component) and acetabular cup uses a digital lateral x-ray of a preferably standing patient to determine a pelvic tilt angle of the patient from the standing x-ray. A virtual hip stem is implanted at an initial stem version angle into a virtual femur. Digitized hip joint motion data from at least one individual moving through one or more typical daily human activities is obtained. Multiple acetabular cup inclination and version angles of a virtually implanted acetabular cup are calculated that avoids impingement between the virtual hip stem implanted at the initial stem version angle while utilizing the hip joint motion data of the at least one individual based on the patient pelvic tilt angle. Preferably, the at least one individual from which the motion data is obtained is the patient receiving the prosthetic hip stem and acetabular cup. Alternately, or in addition, the hip joint motion data is from an average of at least five individuals. The typical daily activities are selected from the group consisting of pivoting on one foot, rolling over in bed, getting in and out of the car, squatting, sitting down in a chair, rising from a chair, picking up an object, climbing up stairs, climbing down stairs, sitting on a toilet, rising from a toilet and walking. Preferably the motion data comprises data from the point in each motion whereas the motion is maximized. (E.g. at lowest point in squat for squat motion).

The virtual hip stem and acetabular cup preferably are selected from a group of commercially available hip stems and acetabular cups.

The data for virtual representation of the hip stem and acetabular cup may be obtained from a computer aided design (CAD) system used for the fabrication of the hip stem and acetabular cup. This data may be stored in the memory of a computer being used to perform the virtual hip stem/cup motion. A safe zone is calculated when calculating the range of inclination and anteversion angles for the virtually implanted acetabular cup. The safe zone being where impingement with the virtually implanted hip stem, which is virtually implanted at the initial stem version angle, is avoided throughout a range of hip joint motion of the one or more typical daily human activities.

BRIEF DESCRIPTION OF THE DRAWINGS

In the description.

FIG. 14 shows the variables utilized by the range of motion software as inputs to calculate cup inclination and cup version;

DETAILED DESCRIPTION

Figure 1:
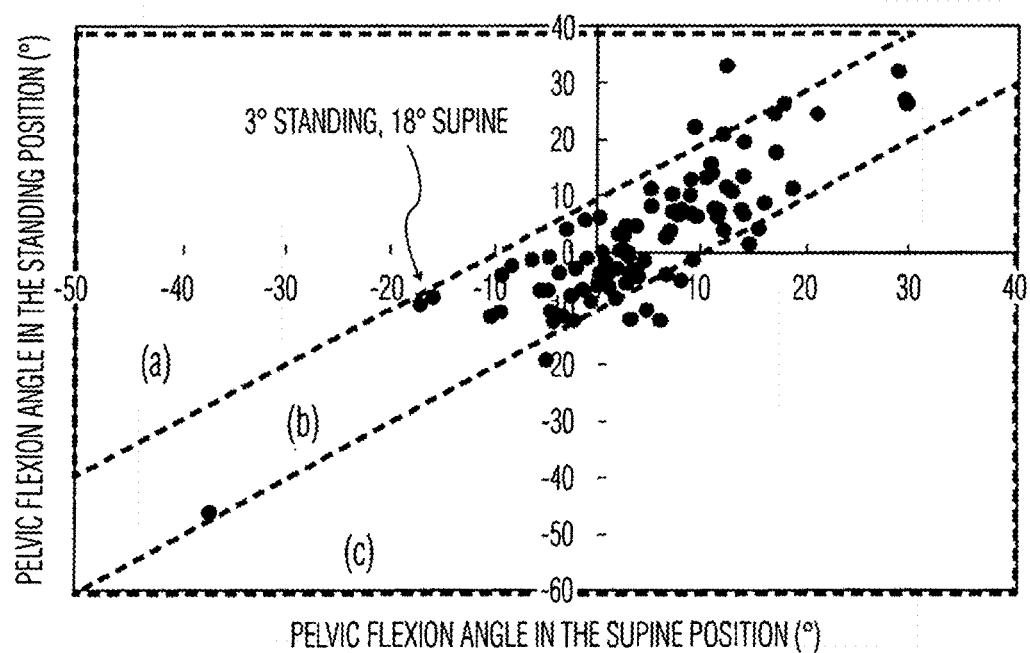
FIG. 1 is a graph showing the relationship between the pelvic flexion angles in the standing position, and the pelvic flexion angle in the supine position.

FIG. 1 is a plot of pelvic flexion angles in the supine position versus those in the standing position. Patients were divided into three groups. There was (a) greater than $10°$ flexion of the pelvis from the supine to the standing position in two of the 101 patients, (b) $10°$ or less pelvic flexion angle in 91 of the 101 patients (shown for example as $3°$ standing and $18°$ supine), and (c) greater than $10°$ extension of the pelvis in eight of the 101 patients.

In current orthopaedic surgery, it is assumed that Pelvic Tilt changes from standing to supine are negligible. That when a patient lays down supine on an operating room (OR) table or to have an anterior-posterior (AP) x-ray taken, or to have a CT taken, that any change in the pelvis flexing forward or backward is negligible.

In reviewing published data on pelvic tilt, these papers show a "general" correlation between standing and supine pelvic flexion (tilt). A point on a $45°$ angle would show that the pelvic tilt of a person when standing did not change at all when the person laid down in a supine position. In this case, a surgeon could use the OR table or the floor as a reference point. If the cup were intended to be implanted at a $40°$ inclination and a $15°$ anteversion with respect to the table, the cup would remain at $40°/15°$ when the person stood up.

However, with the examples shown in FIG. 1 of a pelvic tilt of minus $3°$ standing, and minus $18°$ when the patient was in the supine position, the change in pelvic tilt of $15°$ when the patient is on the operating room table may significantly affect the cup position in the standing position. A cup implanted at 40/15 in the minus $18°$ pelvic position would necessarily be different when measured in the standing position with the pelvis flexed back to the minus $3°$ position. And if the difference is enough to result in stem/cup impingement, then the assumption that pelvic tilt is negligible is incorrect.

Figure 2:
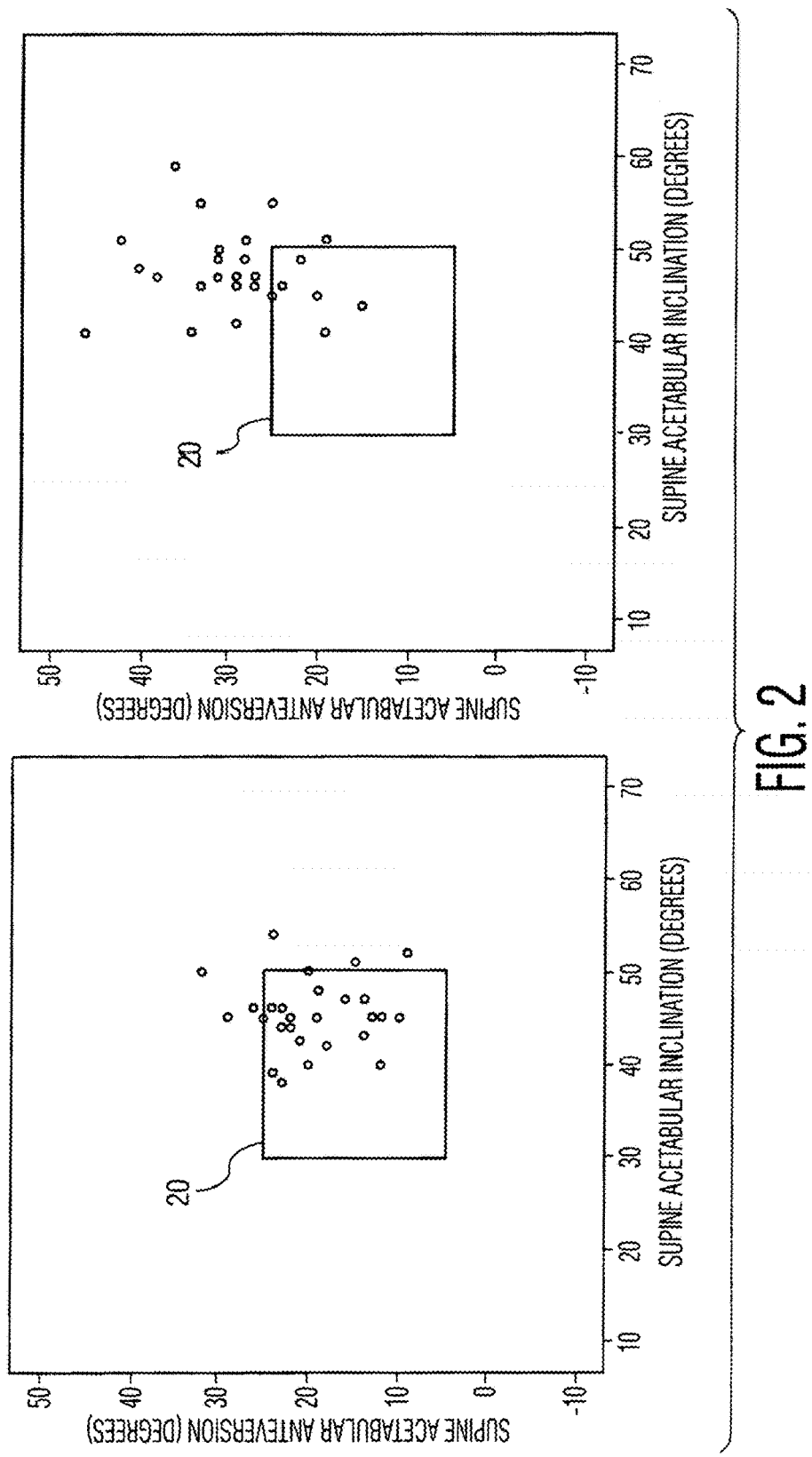
FIG. 2 is the supine and standing acetabular cup orientation in the context of the Lewinnek's Safe Zone (shown as the central square) with the left hand figure showing that 6 of the 30 sample acetabular components were oriented outside the safe zone in supine, while as shown on the right, 22 out of 30 acetabular components were oriented outside the safe zone when standing.

FIG. 2 shows supine and standing acetabular orientation in the context of Lewinnek's safe zone 20 (See Lewinnek G. E., Lewis T. L., Compere C. L., Zimmerman J. R., Dislocation After Total Hip Replacement, Journal of Bone and Joint Surgery Am 1978; 60:217-220.) As shown in FIG. 2, 20% (6 out of 30) of acetabular components were oriented outside the safe zone in supine. In standing the percentage of acetabular components which were oriented outside the safe zone increased to 73% (22 out of 30).

Au et al, Hip International (2014) demonstrates the difference in cup inclination and version between a patient in the supine and standing position. Again, if the difference is enough to result in stem/cup impingement, then the assumption that pelvic tilt is negligible is incorrect. The individual change in pelvic tilt (supine minus standing) varied between $1°$ and $28°$. The mean pelvic tilt was $2.2°±1.39°$ in supine and $-6.8°±1.67°$ in standing with a significant reduction in standing compared to supine of $9.0°±1.27°$ (p<0.0001).

Note that the Lewinnek safe zone 20 (40 deg+/−10 deg Inclination, 15 deg+/−10 deg Anteversion), is a zone described by Lewinnek in 1978 as a zone generally considered safe for cup position to avoid dislocation. This safe zone is still referenced as the target zone as no viable alternative zone has been proposed.

A cadaver lab was conducted to review a femoral stem version angle as compared to the native bone. Stems were implanted by surgeons and the before and after bone/stem angles measured. Two examples one at $13.4°$ anteverted and the other at $6.7°$ retroverted demonstrate how a stem version angle can differ from the native bone. Whether or not the amount of change is significant enough to result in premature stem/cup impingement is also part of this analysis.

In order to determine if varying pelvic tilt and stem version has clinical significance, a study was performed to digitize the actual complex motions of individual subjects. The actual motions represented common actions such as walking, sitting in a chair, getting up from a chair, using the toilet, going up and down stairs, picking up objects, squatting and pivoting.

Figure 3:
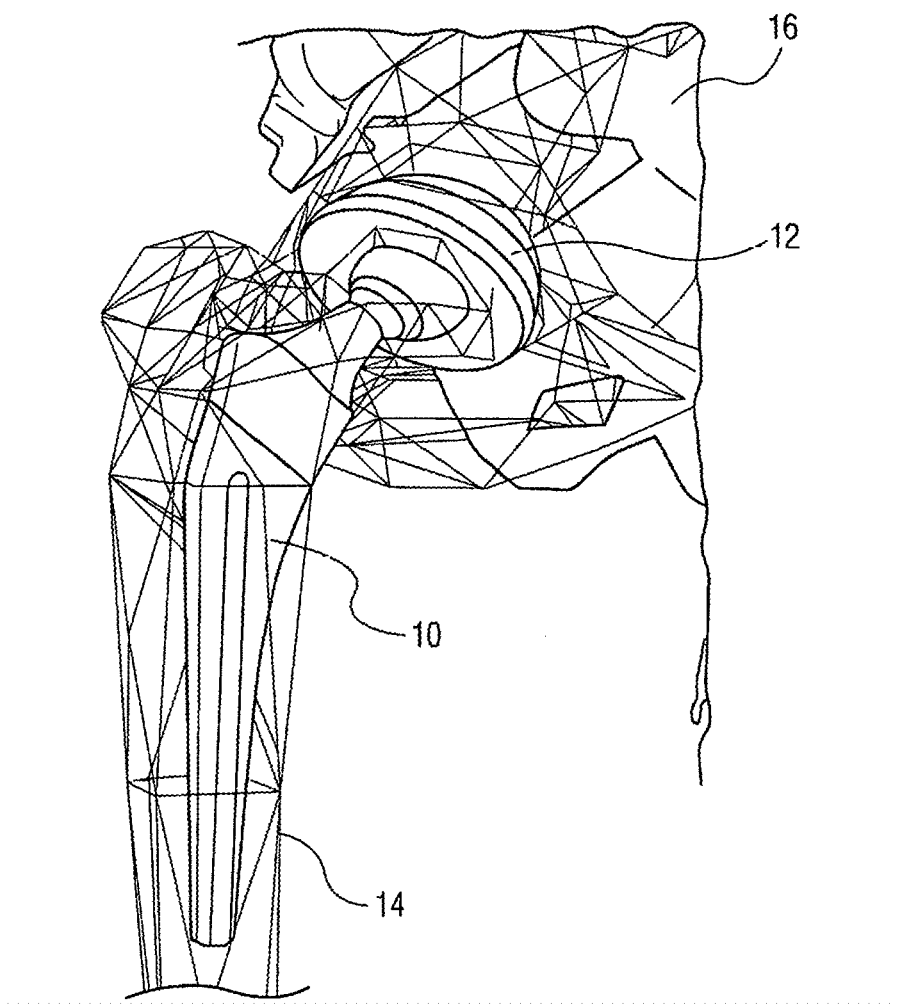
FIG. 3 shows a virtually implanted hip stem (femoral component) and acetabular cup and bearing in a digitally constructed femur and pelvic area.
Figure 4:
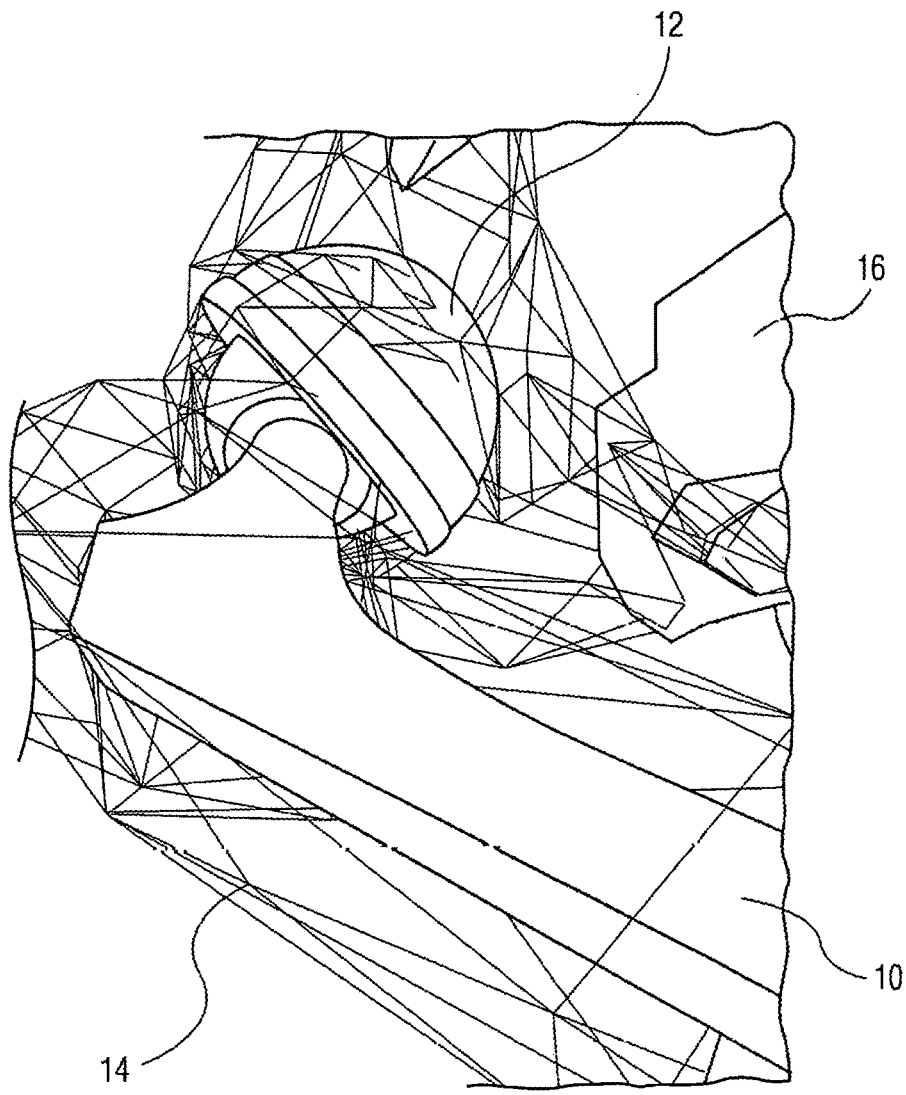
FIG. 4 shows the virtually implanted hip stem and acetabular cup as shown in FIG. 3 rotated to a position during a human activity such as squatting.

Picking up objects and squatting, can potentially lead to posterior dislocation of the hip. Pivoting with a foot planted and the pelvis rotating away can lead to potential anterior dislocation As shown in FIGS. 3 and 4, a range of motion (ROM) software tool was developed to specifically analyze implant impingement and dislocation issues. Virtual implant models can be "implanted" and the bones set to articulate at the specific motions as described above.

As shown in FIGS. 3 and 4, a virtual femoral component 10 and a virtual acetabular component 12 are implanted on a virtual femur 14, and a virtual pelvis 16 respectively. The components 10 and 12 are digital representations of commercially available components with the femur and pelvis constructed from digital x-ray or CT data of the patient. Note: with component/component impingement analysis, the bone geometry is not important and can be virtual bones, not those of the patient. If also looking for component/bone and bone/bone impingement, then actual patient data is needed and obtained preferably from CT data.

The range of motion (ROM) tool uses a hip ROM simulator which computes and animates hip range of motion as a function of implant geometry, implant alignment, and patient activity. The user is provided a three-dimensional model of the skeletal system that contains anatomic coordinate systems for the pelvis and femur. See FIGS. 3 and 4. For the pelvis, the coordinate system is developed based on the right and left Anterior Superior Iliac Spine (ASIS) and the pubic symphysis. The orientation of this coordinate system can be modified by specifying a pelvic tilt parameter (see U.S. 2015/0088145), defined as the angle between a plane containing both ASIS and the pubic symphysis (the anterior pelvic plane, APP) and a global vertical plane or Coronal plane. CAD models of hip implants can be imported into the model and positioned in any desired orientation about the anatomic coordinate systems. The software can then compute minimum clearances between the components for any hip position, report total hip range of motion (ROM) in flexion/extension, abduction/adduction, and internal/external rotation during standing, and compute the remaining ROM of the joint at regular intervals during eight functional activities of the joint based on the motion data. Motion data for the eight typical activities (see above) were obtained from gait analyses performed on ten healthy subjects. The software reports ROM as femoral component and acetabular cup undergo the amount of motion attainable before component—component impingement occurs. Range of motion may be assessed on a standard stem with a 132° neck angle and a 36 mm head articulating with a 36 mm liner in a 54 mm acetabular shell (Stryker Orthopaedics, Mahwah, N.J.). Inclination of the cup is set to 45° and anteversion to 20°.

The implants are imported into the software as STL files. The surface of the models are made up of varying sized triangles that form the outer surface shape. If there is a large flat, then a few large triangles are used. If there is curved or complicated surfaces, then very small triangles are used. The software takes about 20-30 minutes to run each time as it compares each triangle of one part with each of the other. The software then color codes the triangles per a color bar guide. The color bar guide denotes the amount of clearance for each color, from zero (impingement) to greater than 10 mm.

The graphs in FIGS. 5 through 10 show the lines crossing from a motion from 0 to 100%, the software holds all the variables fixed at a percent of ROM, and just vary one variable to find the limits (the bold lines in FIGS. 6-10). So for instance, at 50% motion on squatting, and looking for the bold lines that represent the limits of Flexion/Extension, it will hold all variables at 50% fixed and vary first in flexion for one bold line, then extension for the other. At 51%, it does the same, etc. If the central light black line 60 for the actual human ROM crosses a bold line 62 or 64, then it shows that if there were implants in the human, they would impinge for the full length of where the bold lines 62, 64 cross over or contact the light line 60.

Figure 5:
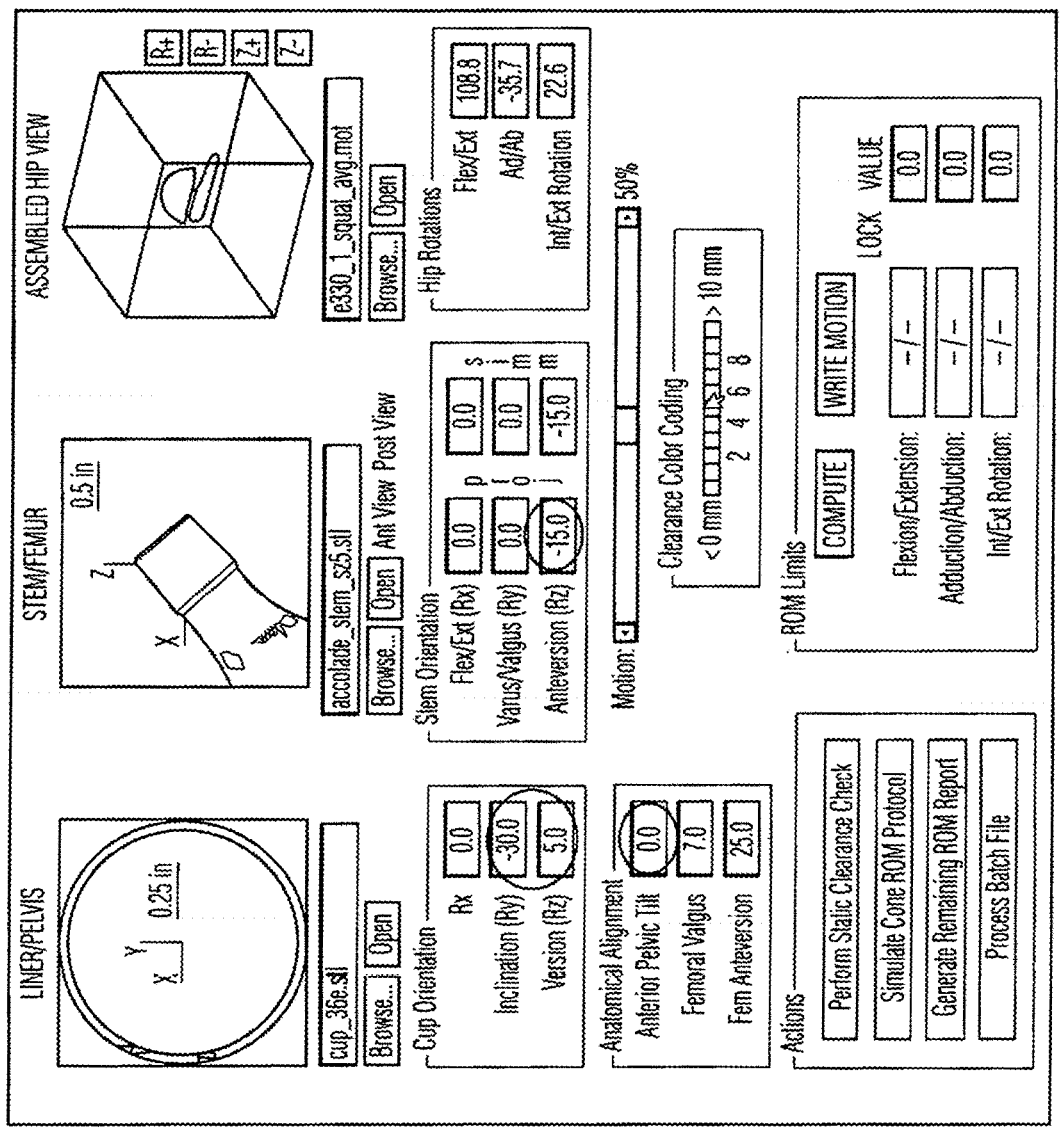
FIG. 5 is an example of a data input screen for a range of motion software tool for a 0° pelvic tilt with a virtual stem implanted at 15° anteversion and a cup having 30° inclination and 5° version for a first subject.

In FIG. 5, the computer model allows the user to set variables which includes stem version, pelvic tilt, cup inclination and anteversion, etc. The user then chooses the implant types and simulated motion which would be the exact motion of the human subjects who were digitized. (FIG. 5 shows a squat motion was used).

Figure 6:
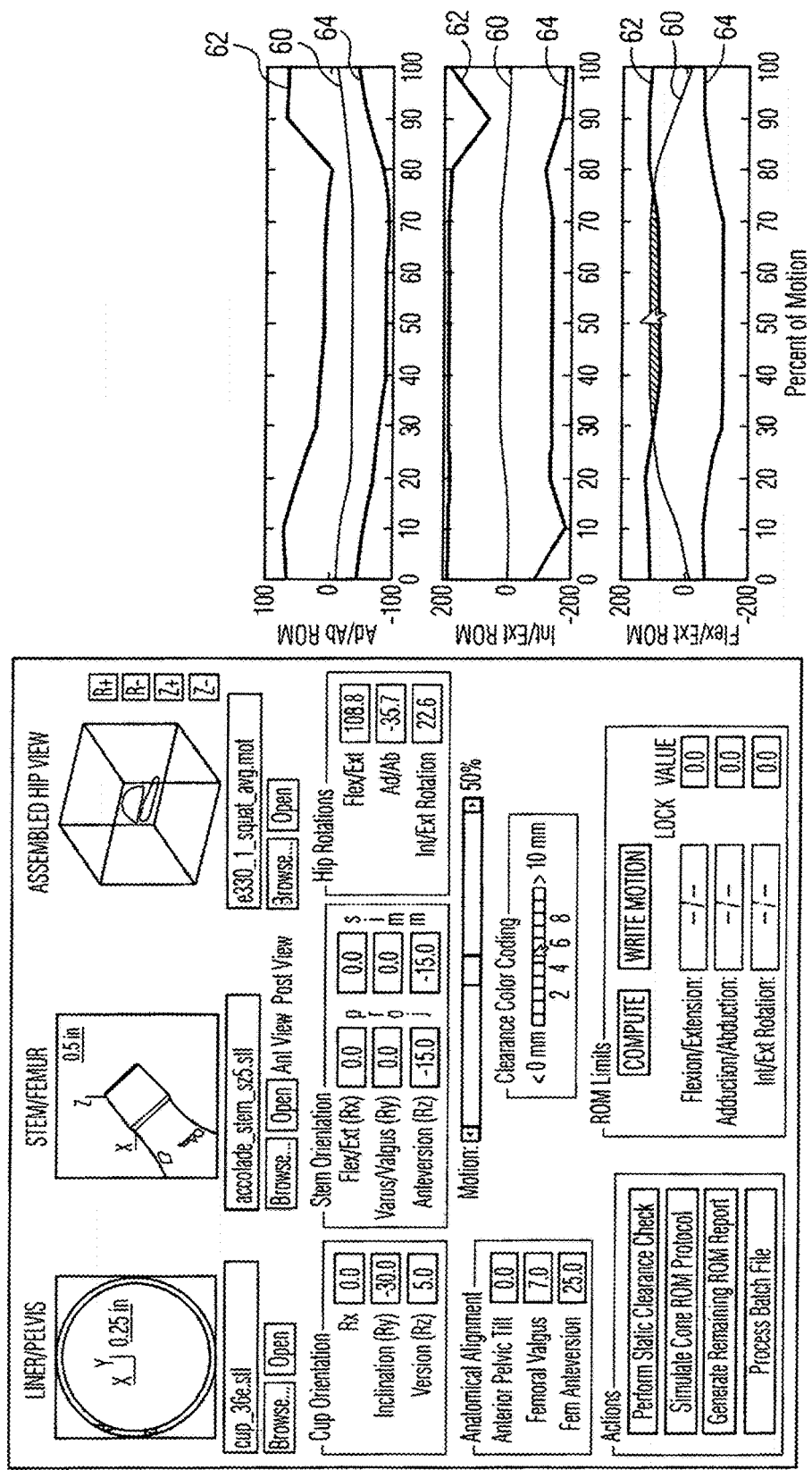
FIG. 6 is the output of the range of motion tool with an inputs of FIG. 5 going through 50% of a squatting motion showing a impingment between 30° and 75° flexion/extension range of motion which occurs during squatting.

As shown in FIGS. 6-10, the ROM tool will calculate whether the stem will impinge on the cup when put through a motion, in the example of FIG. 6, a squatting motion. The exact squatting motion of the human subjects is simulated. Impingement can be determined by comparing the chart representing clearance to the locations shown on the cup rim and stem neck. It can also be determined by observing if the lines cross in the graphs to the right. In looking at the Flexion/Extension ROM vs Percent of Motion graph, the light black line, representing the human subject, crossed over the dark black line, representing the portion of the percent of motion where impingement occurs (approximately from 30-75% of the squatting motion) as shown in FIG. 6.

Figure 7:
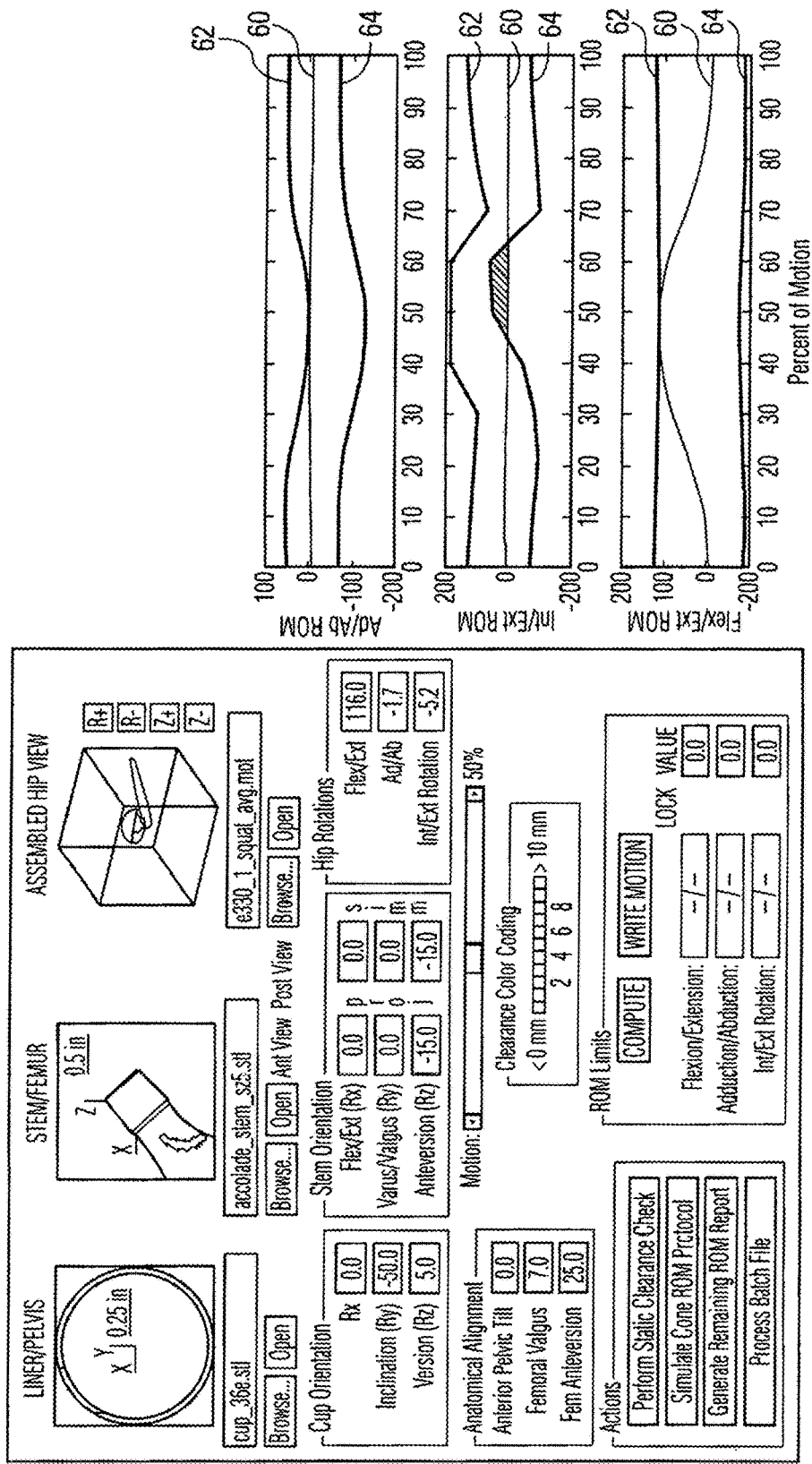
FIG. 7 shows a 0° pelvic tilt, 15° stem version, 50° cup inclination and 5° cup version during a pick-up motion showing impingement occurring between 40° and 65° of motion in obduction, aduction, internal/external rotation, and flexion extension.

In the example of FIG. 7, a specific cup and stem was used, and Pelvic Tilt (0 deg), Stem Version (15 deg), Cup Inclination (50 deg), and Cup Anteversion (5 deg) were all set. This combination resulted in impingement as indicated by the graphs of FIG. 7.

Figure 8:
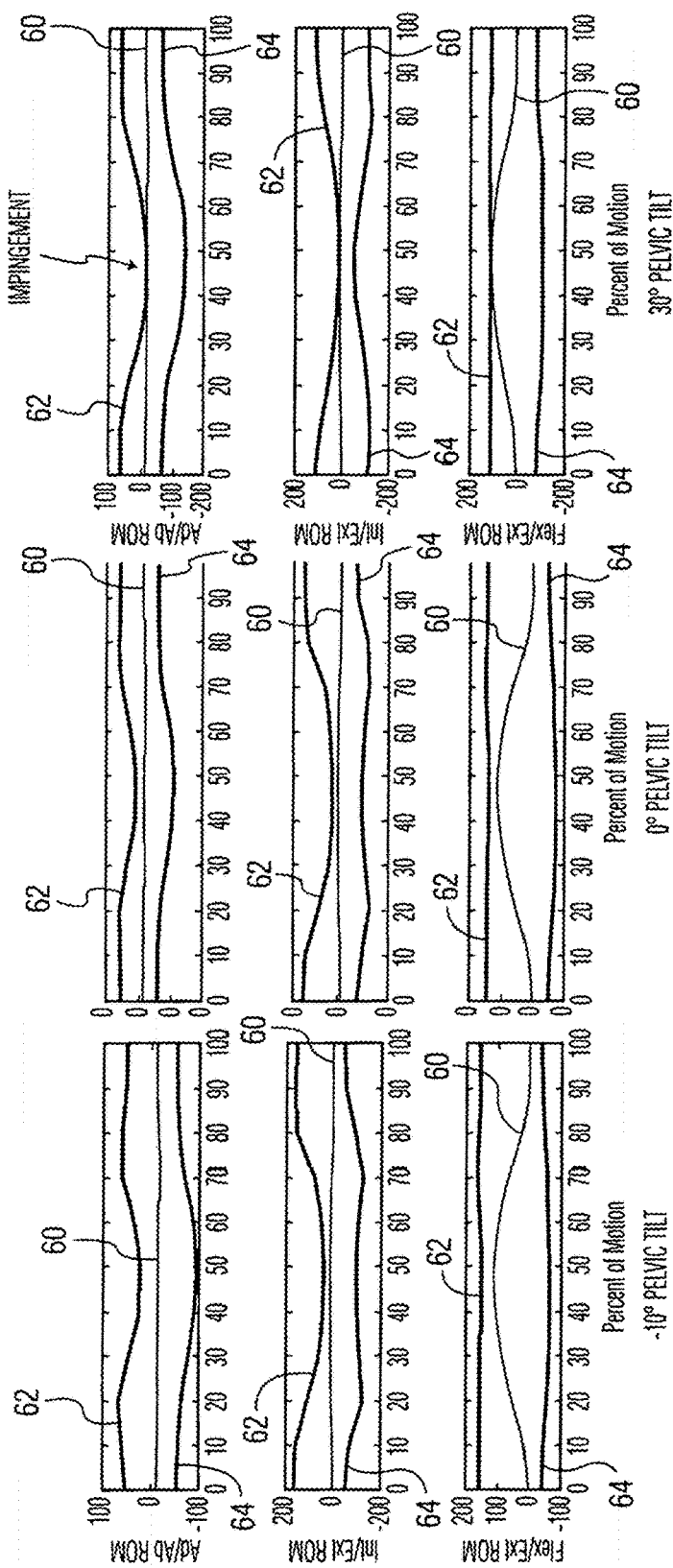
FIG. 8 is the output of the range of motion tool during picking up of an object at 0° pelvic tilt, −10° of tilt and 30° pelvic tilt showing impingement occurring in an individual with 30° pelvic tilt.

FIG. 8 shows how just changing the pelvic tilt eventually results in impingement. In FIG. 8, three pelvic tilt angles are used to calculate the range of motion for one or an average of more individuals, picking up an object. At 30° pelvic tilt contact occurs where lines 60 and 62 are tangent.

Figure 9:
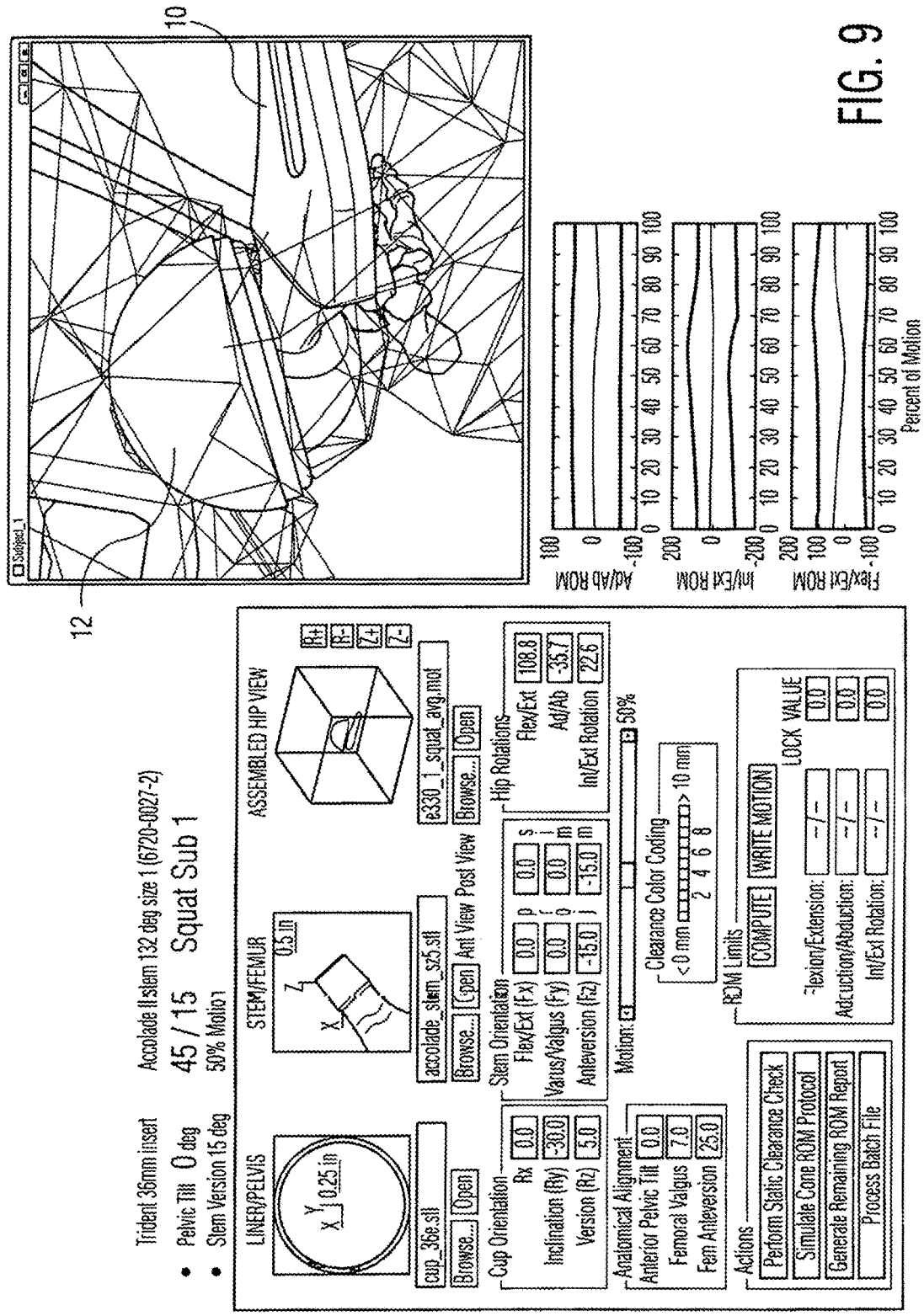
FIG. 9 shows a squatting motion of a first subject at 0° pelvic tilt, 15° stem version and 45° cup inclination and 15° cup version showing a clearance between cup 12 and stem 10 throughout the entire range of motion.
Figure 10:
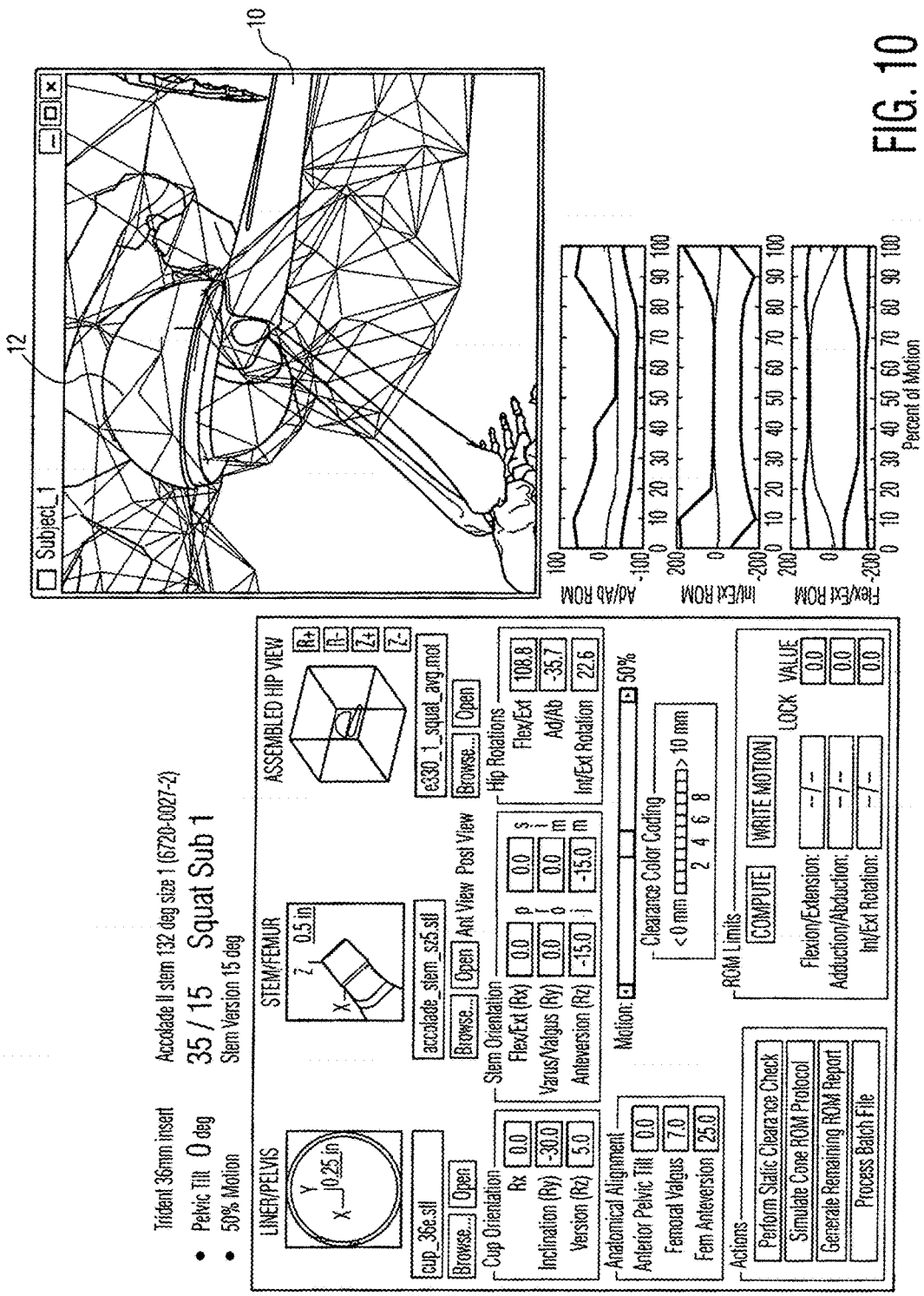
FIG. 10 shows an example of impingement between the cup 12 and the stem 10 assuming a pelvic tilt of 0°, a femoral stem version of 15°, a cup inclination of 35°, and a cup version of 15°.

The ROM software tool also allows for visual observation on a computer display of clearance between femoral component 10 and cup 12 as shown in FIG. 9 on a display monitor, or of impingement (See FIG. 10).

Figure 11:
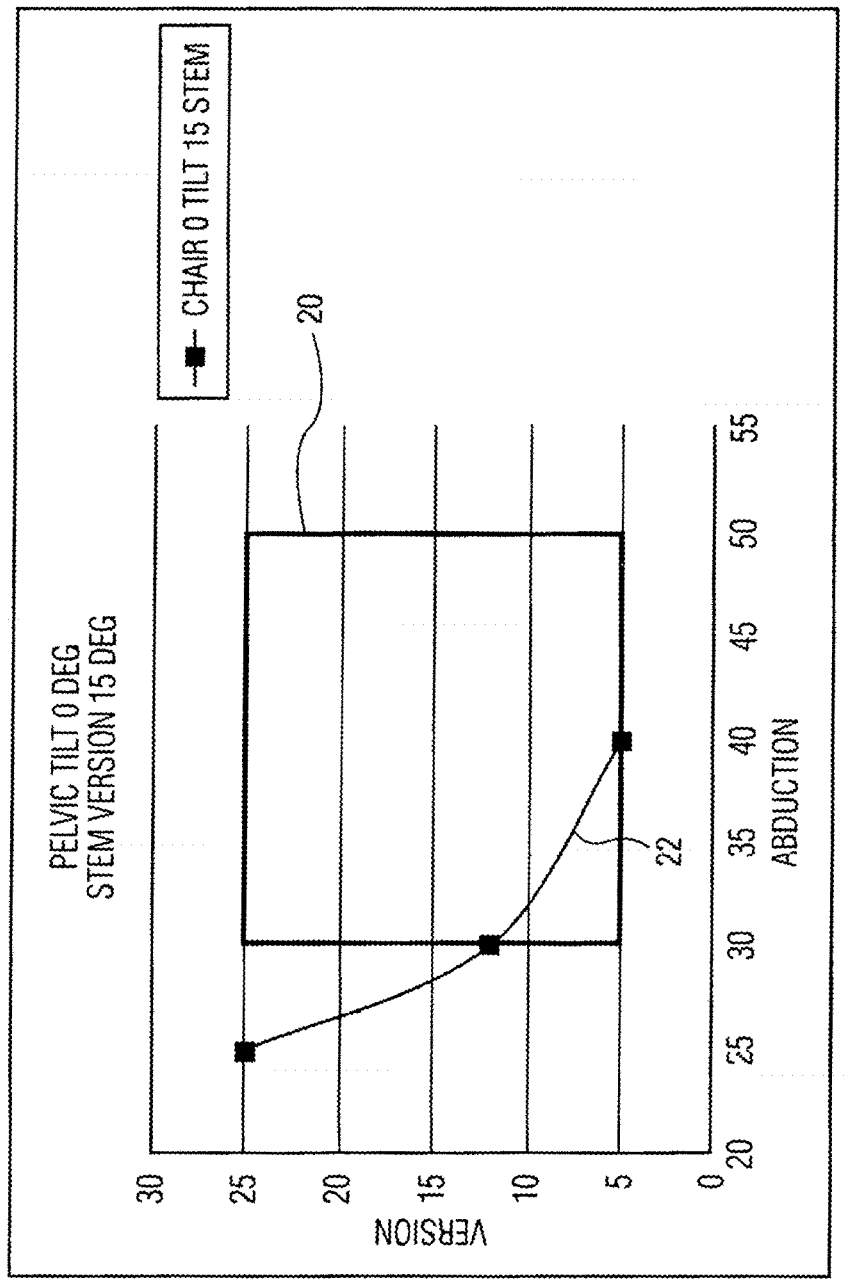
FIG. 11 shows a caculated line of contact assuming 0° pelvic tilt and 15° stem version during sitting in a chair with impingement occurring and inclinations of less that 40°, inversions above 5°.

The ROM tool software was developed to find out at what specific abduction and version angles result in stem/cup impingement. In FIG. 11, The Lewinnek Safe Zone 20 is shown for reference. These figures show plots of impinge during a single motion. Initiation of impingement for specific stem and cup implants, Pelvic Tilt of 0 deg, Stem Version of 15 deg, and rising from a chair motion 22 is shown in FIG. 11.

Figure 12:
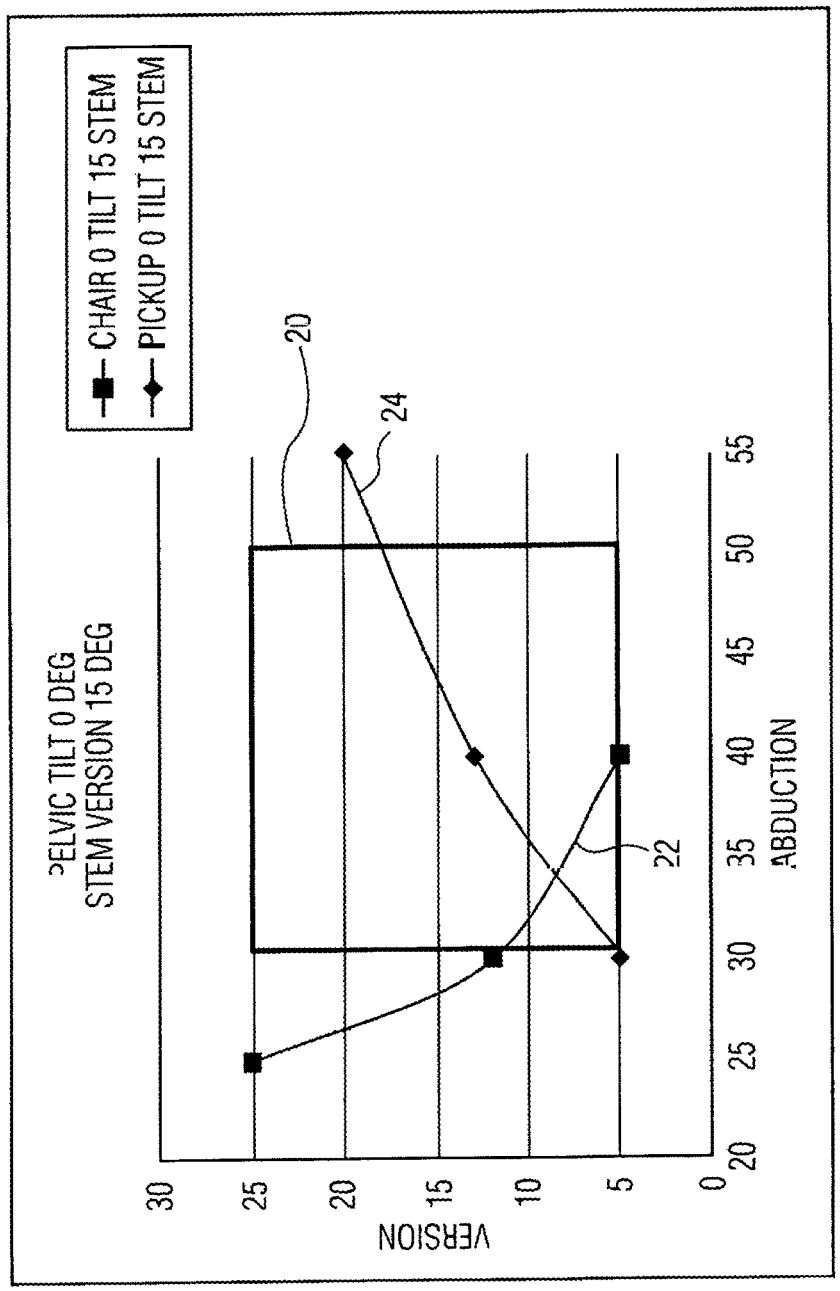
FIG. 12 modifies the calculated safe zone by adding in the pick-up motion based on the same inputs as in FIG. 11.

Adding picking up an object motion 24 to the same graph might overlap as shown in FIG. 12.

Figure 13:
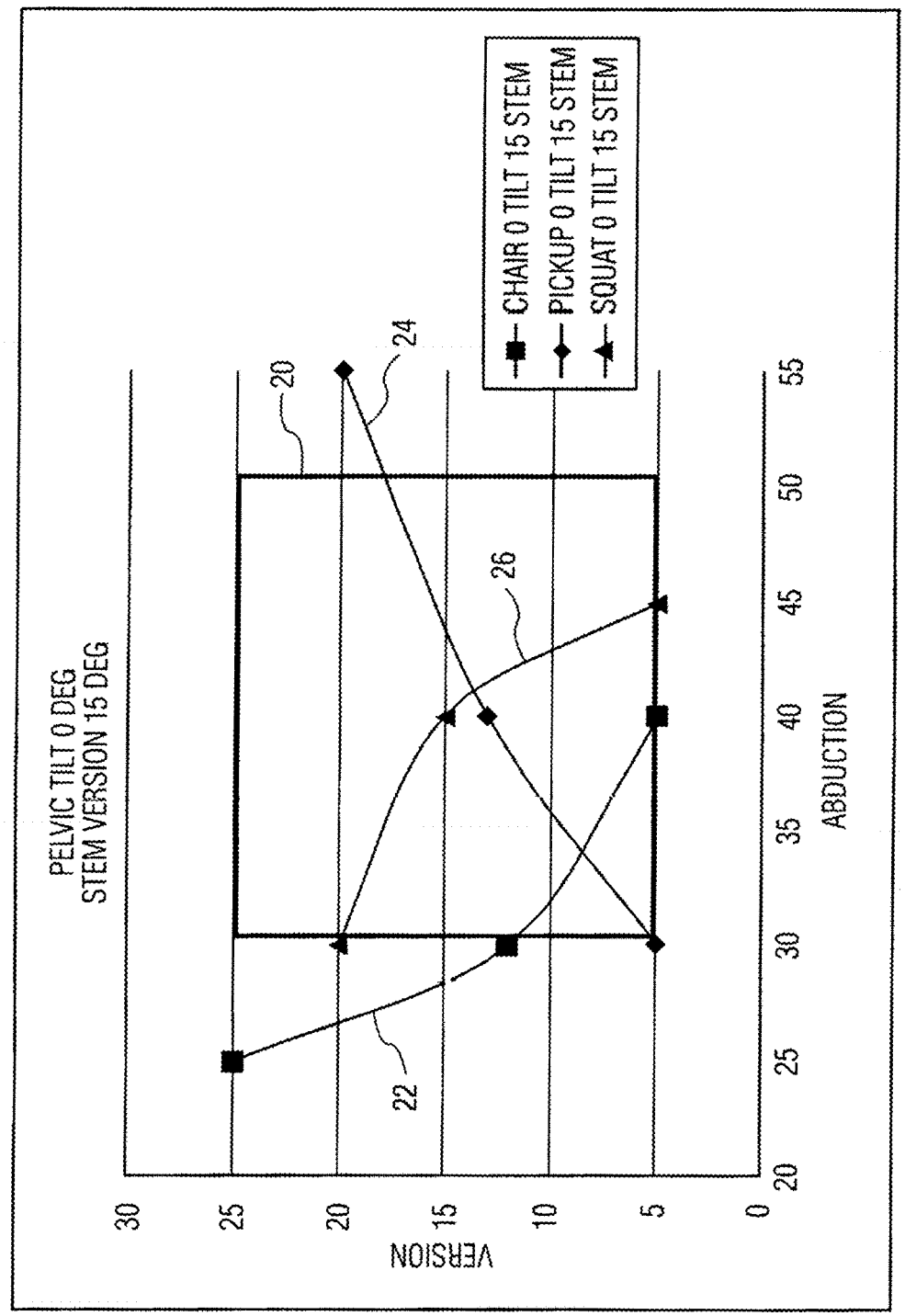
FIG. 13 further modifies FIGS. 11 and 12 by adding in a squatting motion, thus showing three curves indicating where impingement occurs between the femoral component and the implanted acetabular cup.

FIG. 13 adds the squatting motion 26. Reviewing all the motions together helps to define combined areas of impingement and non-impingement.

Figure 15:
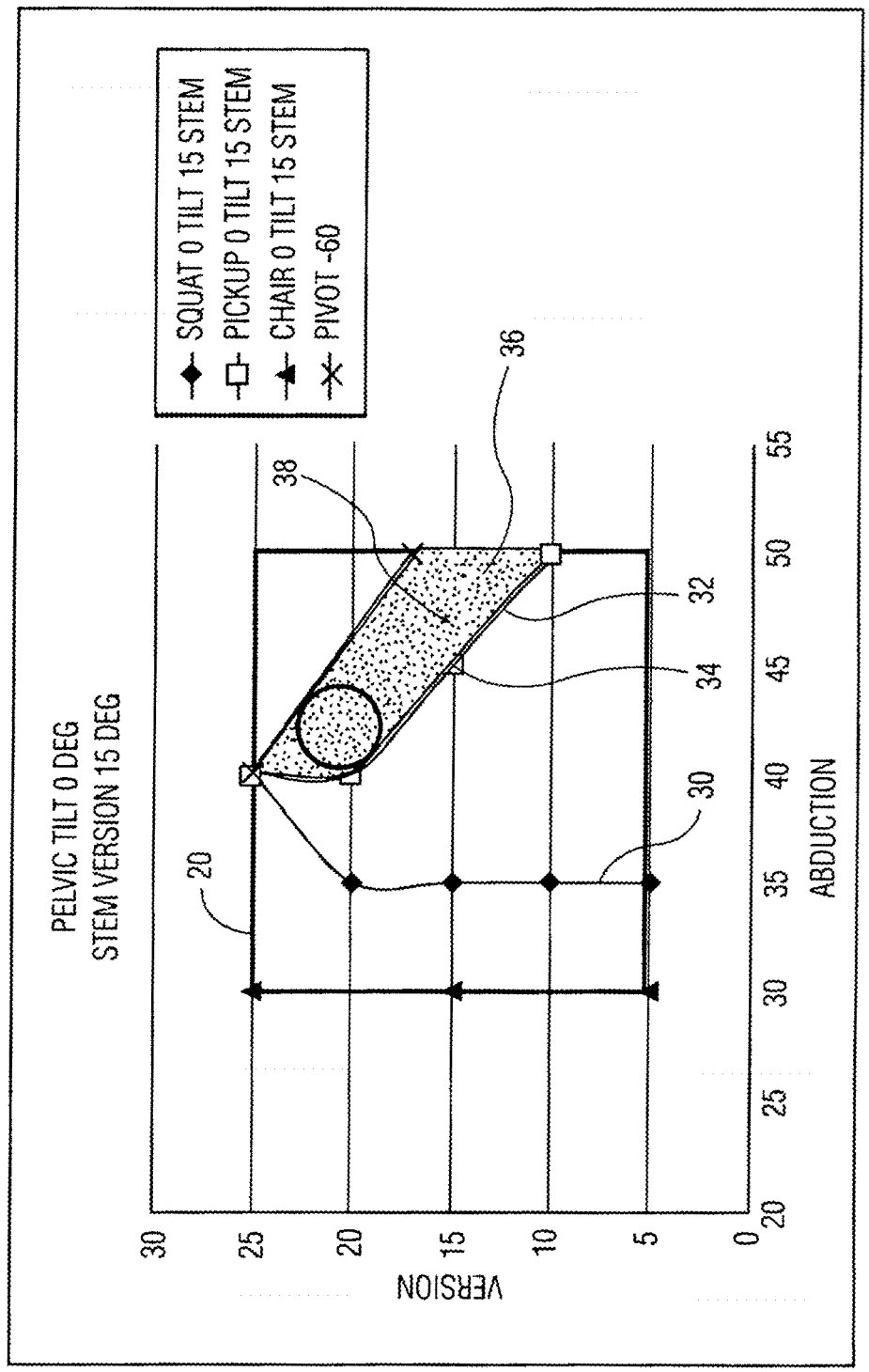
FIGS. 15-16C show caculations of safe zones based on the acetabular cup inclination (abduction) inversion based on various pelvic tilt inputs and femoral stem versions with regard to various motions such as squatting, pick-up, sitting and getting out of a chair and pivoting.

An example using actual implant models, and realistic variable of Pelvic Tilt and Stem Version amounts are shown in FIG. 14, results in the graph shown in FIG. 15.

FIG. 15 shows squat 30, pickup 32, chair motion 34 and pivot motion 36 resulting in a save zone 38.

Using data from FIG. 14, the curve plots for different motions are shown where impingement starts to occur. The area to the left of the pickup curve 32 represents impingement with potential posterior dislocation. The area to the right of the pivot curve 36 represents impingement with potential anterior dislocation. The shaded area between the two represents a non-impingement "Safe Zone" 38 for this specific implant combination, Pelvic Tilt, and Stem Version. Safe Zone 38 is quite a bit smaller than the Lewinnek safe zone 20 and demonstrates how the variables affect the size and shape of the safe zone.

Figure 16A:
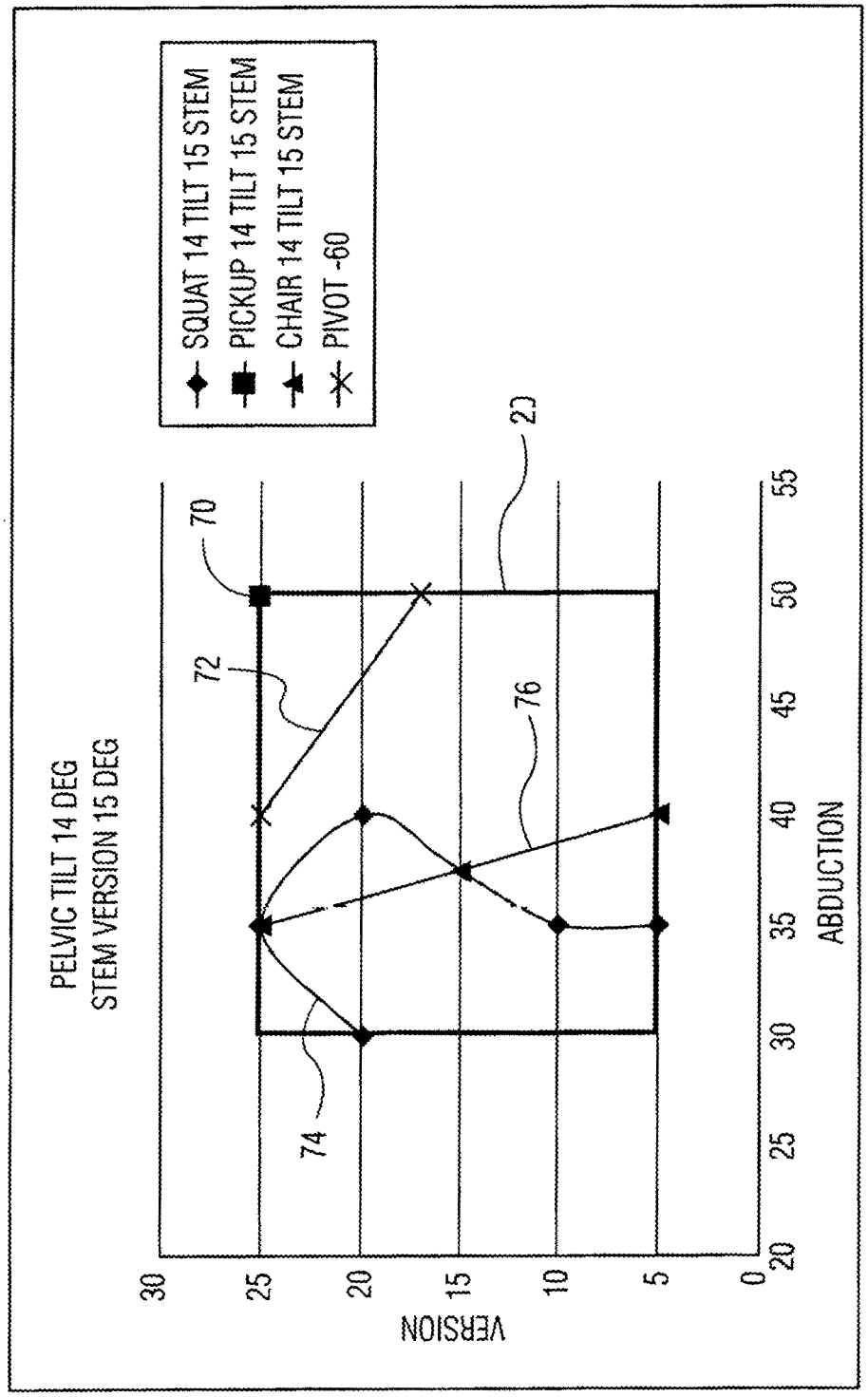
Figure 16B:
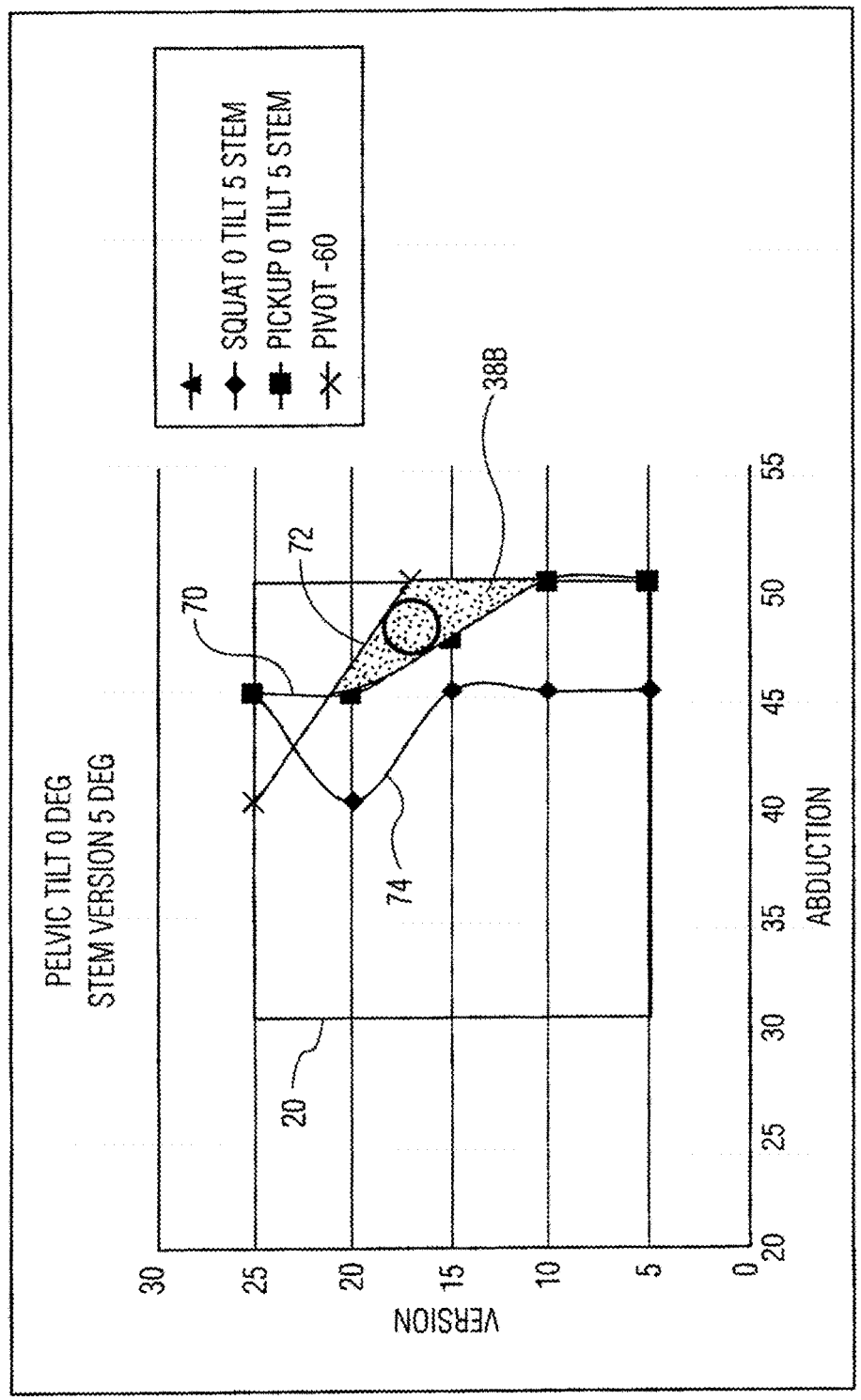
Figure 16C:
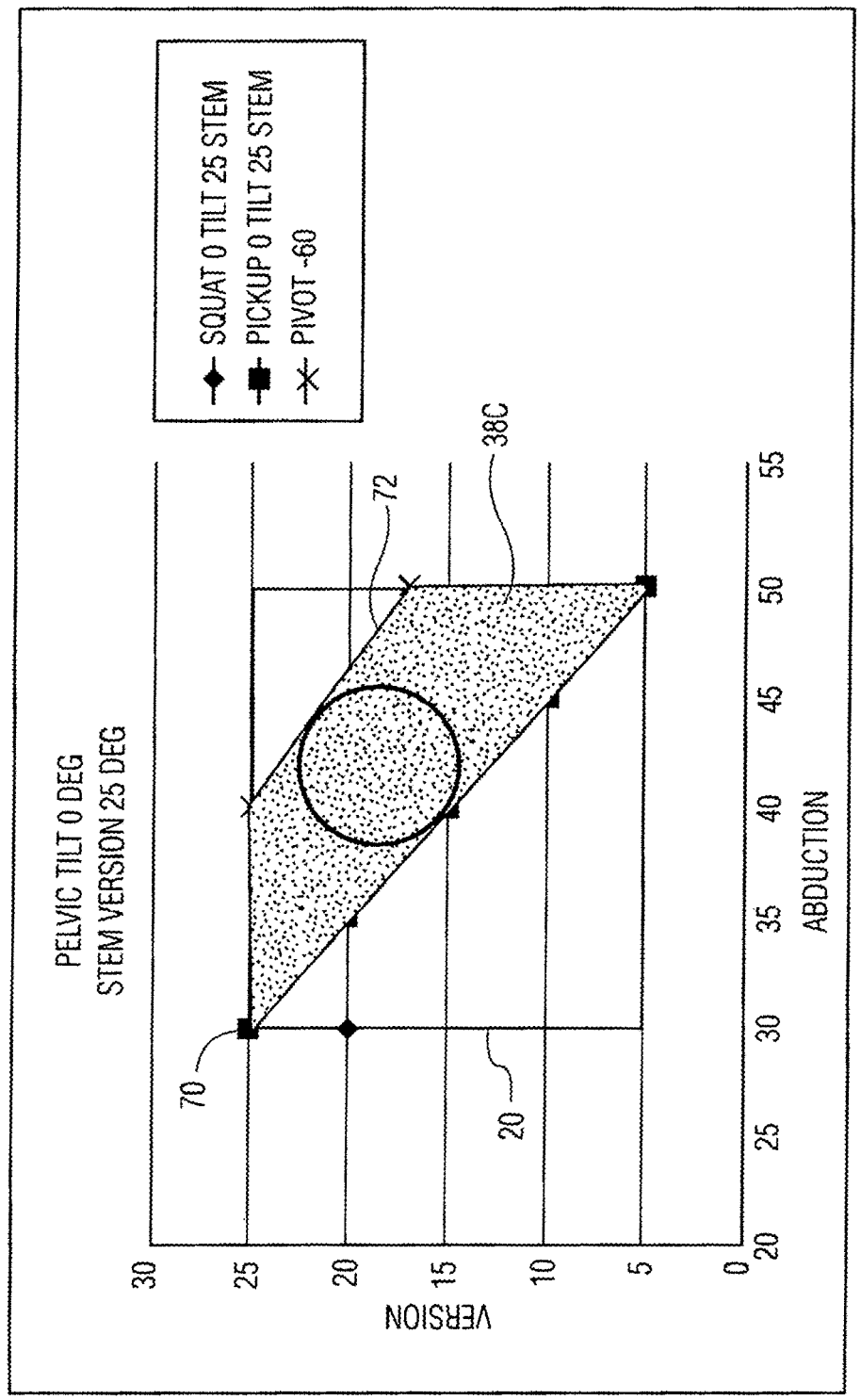

FIGS. 16A to 16C show the new safe zone 38A through 38C respectively is patient specific, as each individual will have their own pelvic tilt and stem version, coupled with implants chosen for that patient. FIGS. 16A-C further demonstrates how the safe zone 38A through C would change with given parameters. This is significant as no currently available cup alignment system takes the Pelvic Tilt into account to determine the safe zone, yet it is very clinically important to do so.

FIG. 16B has a safe zone 38B (shaded area) and FIG. 16C has a safe zone 38C (shaded area).

The method of the present invention allows the surgeon to choose motions that matter. (e.g. squatting for Asian population or gardeners). The surgeon can decide on implant types based on motions (e.g. large or small head sizes, stems with variable neck version options). The surgeon will know the boundaries of adjusting cup position, which is important to balance the need to avoid iliopsoas tendon impingement with cup rim and high-wear inclination angles.

Given this enhanced knowledge of how specific motions and input variables affect the safe zone, a surgeon could choose the motions that matter to the patient when performing surgery. For instance, squatting information could be taken into account for someone that gardens, yet possibly may be disregarded for someone that will not be squatting. Also, knowing that a patient is a yoga instructor may influence a surgeon on the implant type and orientation to use.

Surgeons like to place acetabular cups such that the rim of the cup does not extend into the iliopsoas notch. This could cause the iliopsoas tendon to rub on the edge of the cup, causing pain. With access to the graph of the safe zone while in surgery, the surgeon would have confidence that a cup placed to avoid the iliopsoas notch is also still in the safe zone.

This novel yet practical approach to finding a "safe zone" shows that the safe zone of the present invention is smaller than the Lewinnek safe zone, and explains why a high proportion of dislocations do occur with cups positioned in the Lewinnek safe zone. Better ways of targeting this new safe zone could be done with robotics.

The method demonstrates the clinical need to measure the natural standing pelvic tilt and the stem orientation.

A surgical technique includes measuring patient "Natural" pelvic tilt, taking a lateral digital x-ray image that provides Anterior-posterior plane (APP) vs. Coronal plane angle. Note a surgical technique includes the lateral images commonly taken prior to spine surgery.

Figure 17:
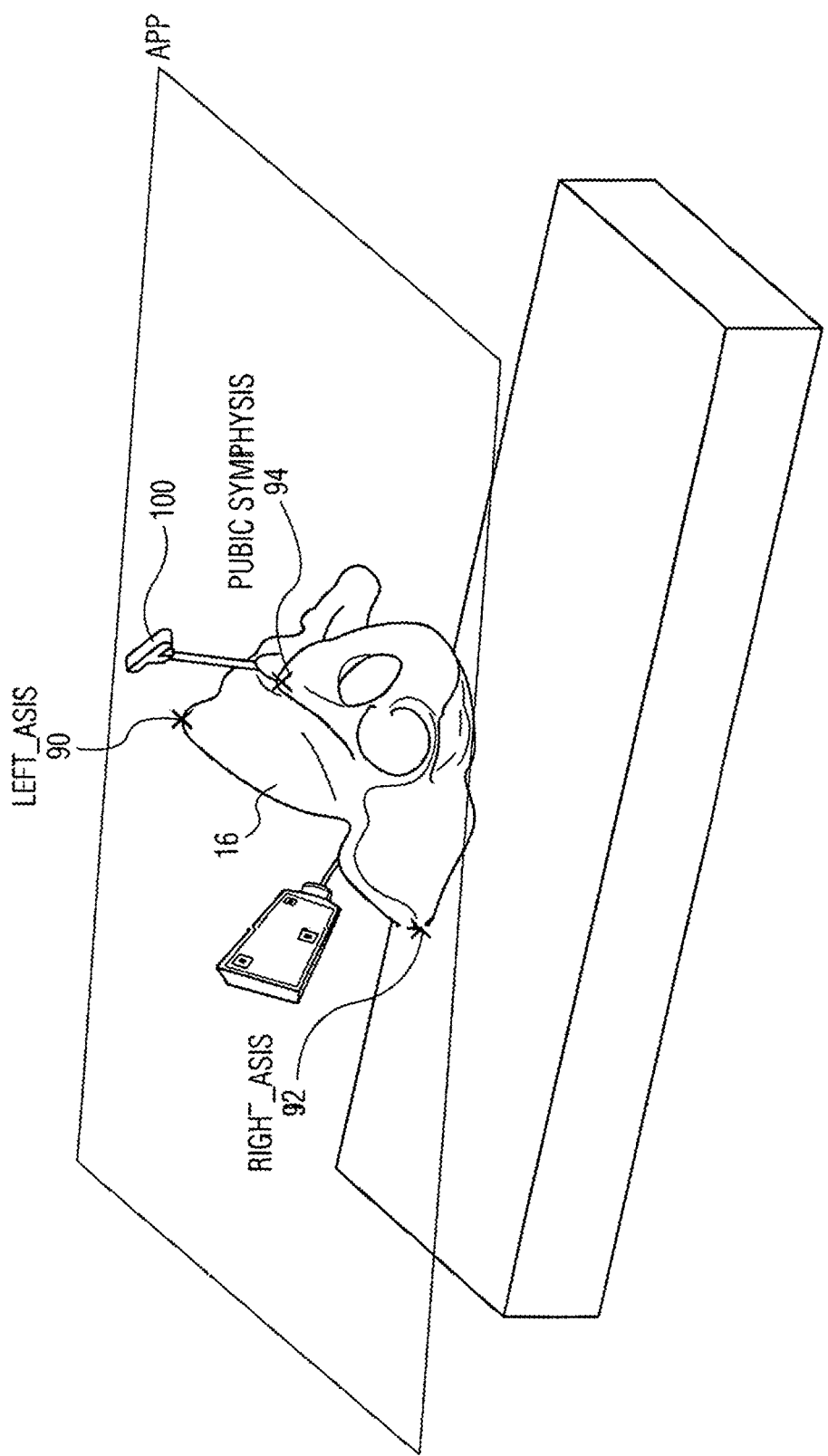
FIGS. 17-21 show a surgical technique which utilizes the outputs defining in the safe zone for implanting an acetabular cup with inclination angles and version angles falling within the caculated safe zone.

FIG. 17 shows the Anterior Pelvic Plane (APP) of pelvis 16 using the right and left ASIS 90, 92 and pubic symphysis 94 also shown in a navigation system pelvic tracker 100 usable with a typical (optical) operating room navigation system. Placing a navigation tracker on pelvis also insures that pelvic movement during surgery is addressed.

Figure 18:
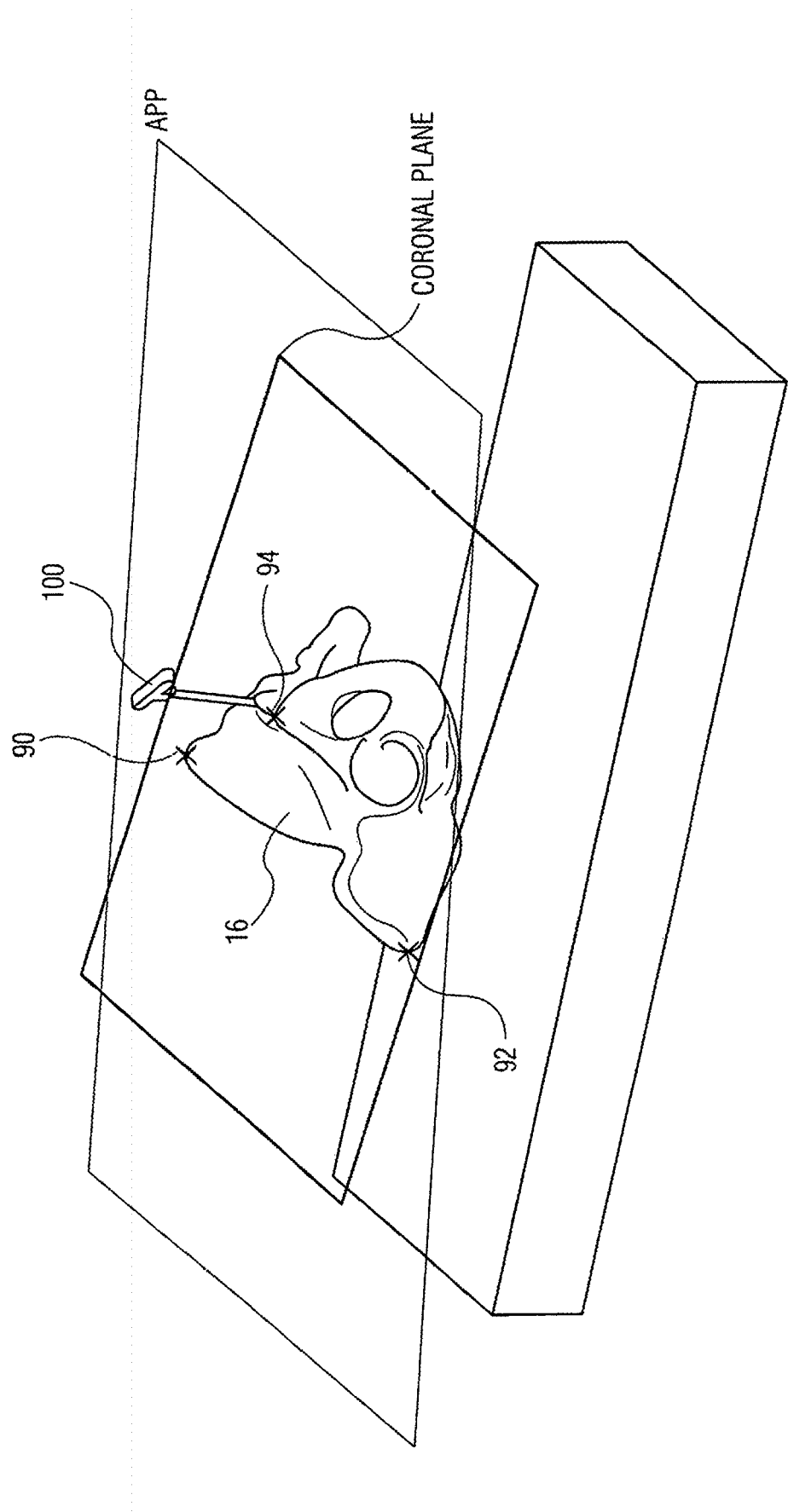

FIG. 18 shows the standing Coronal plane is recreated by finding the APP plane, and knowing that the Coronal plane is the same angle off the APP plane as measured from the lateral image.

Figure 19:
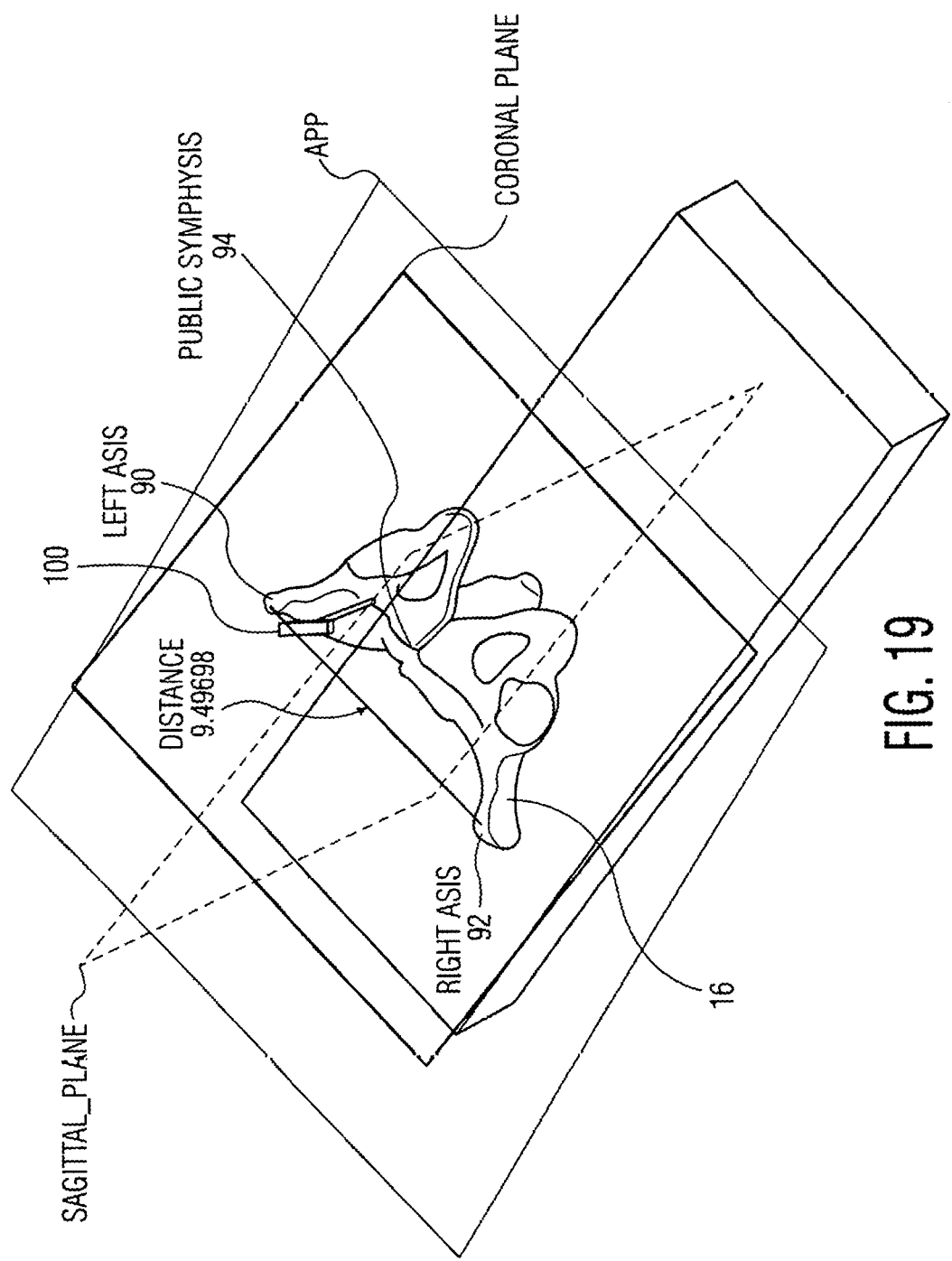

FIG. 19 shows the Sagittal plane as being perpendicular to the Coronal plane and midway between the two ASIS points and/or thru the pubic symphysis.

Figure 20:
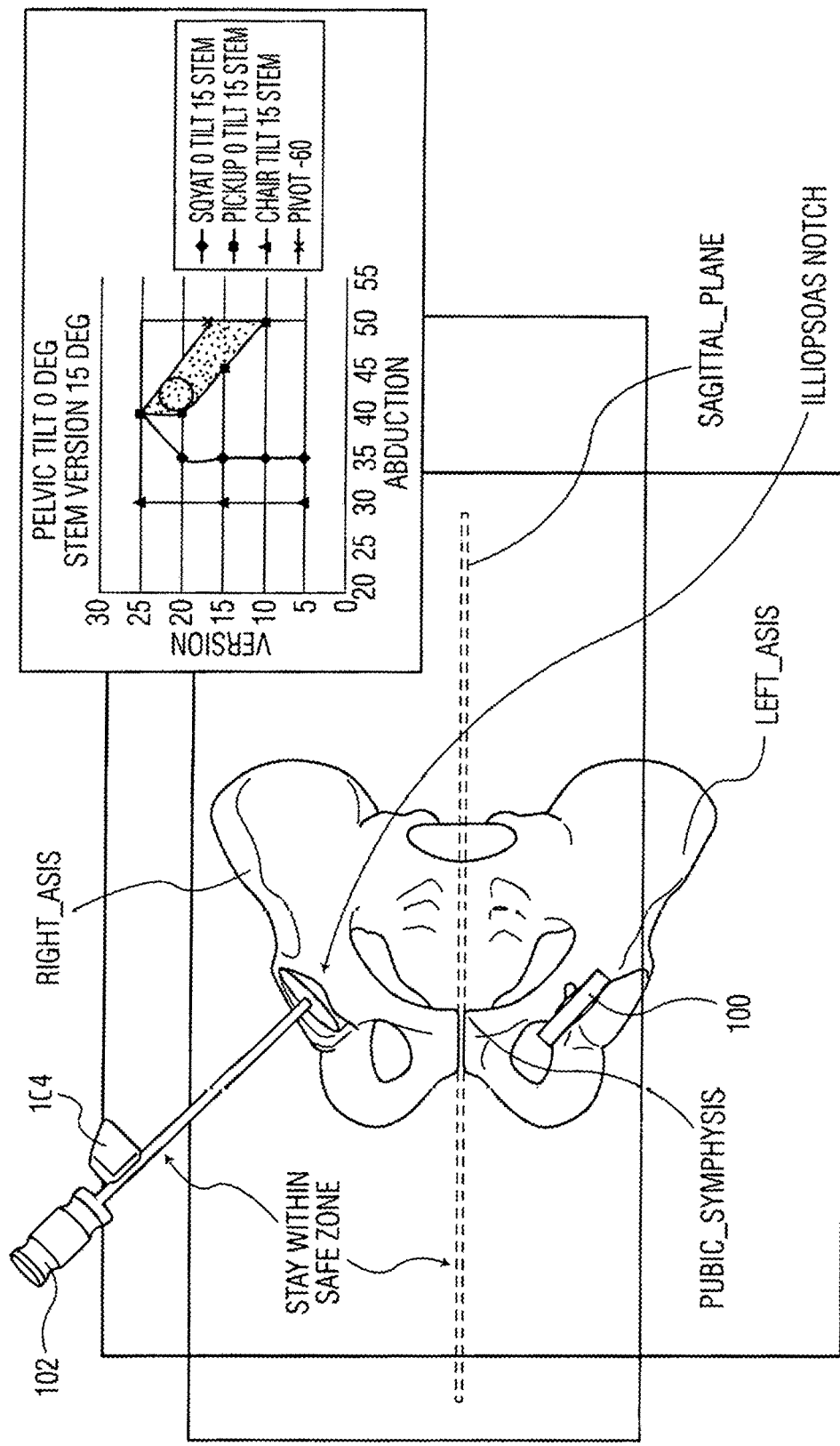
Figure 21:
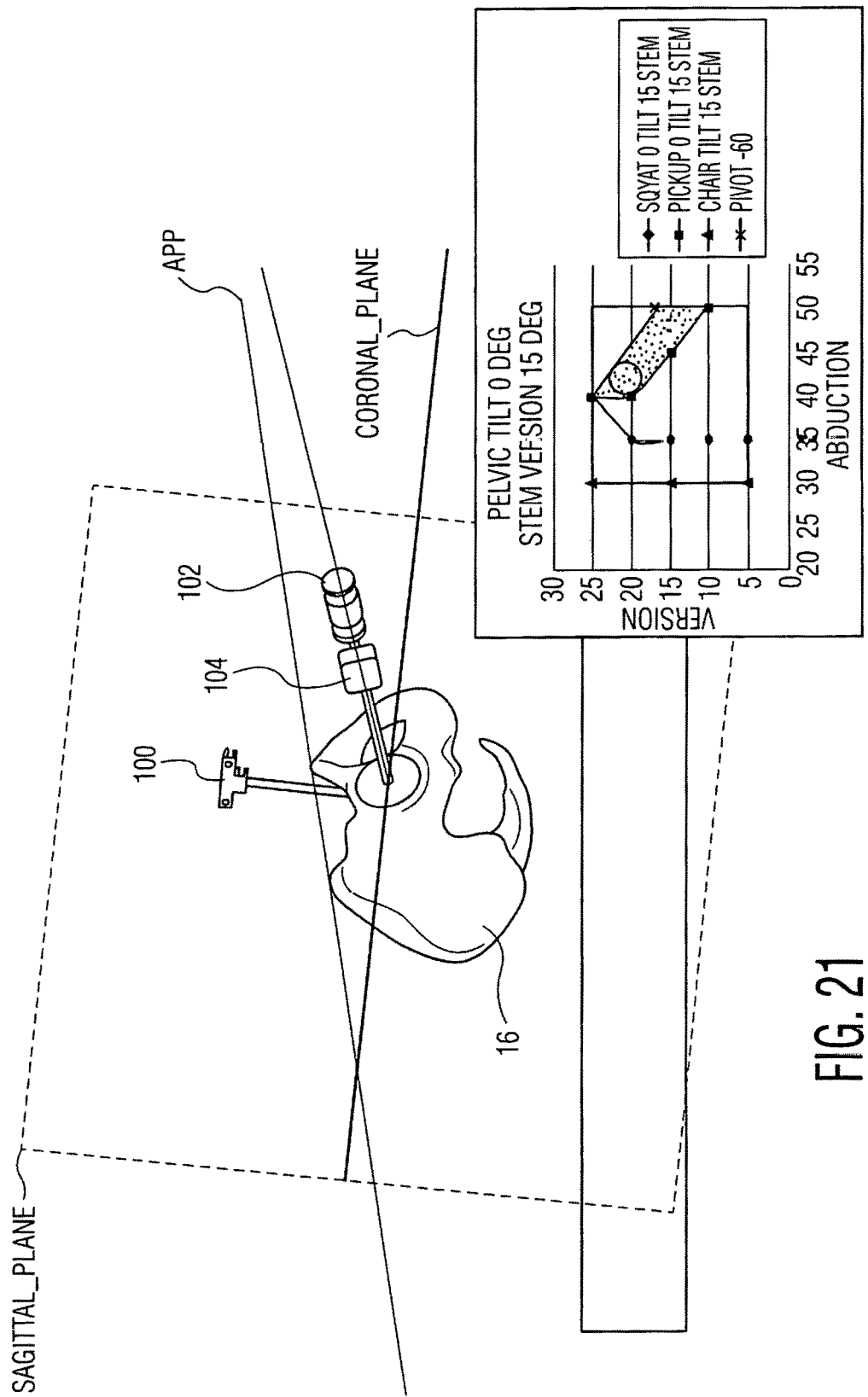

FIG. 20 shows pelvic tracker 100 and an impactor 102 having a tracker 104 therein which guides the impactor to the abduction angle in coronal plane and, as shown in FIG. 21 guides the impactor parallel to sagittal plane to the desired version angle. (See U.S. Patent Publication 2015/0088145 for details).

FIG. 21 shows the cup inserter/impactor aligned with respect to the coronal and sagittal planes to produce cup abduction (inclination) and version angles within the "safe zone" of FIG. 15.

Figure 22:
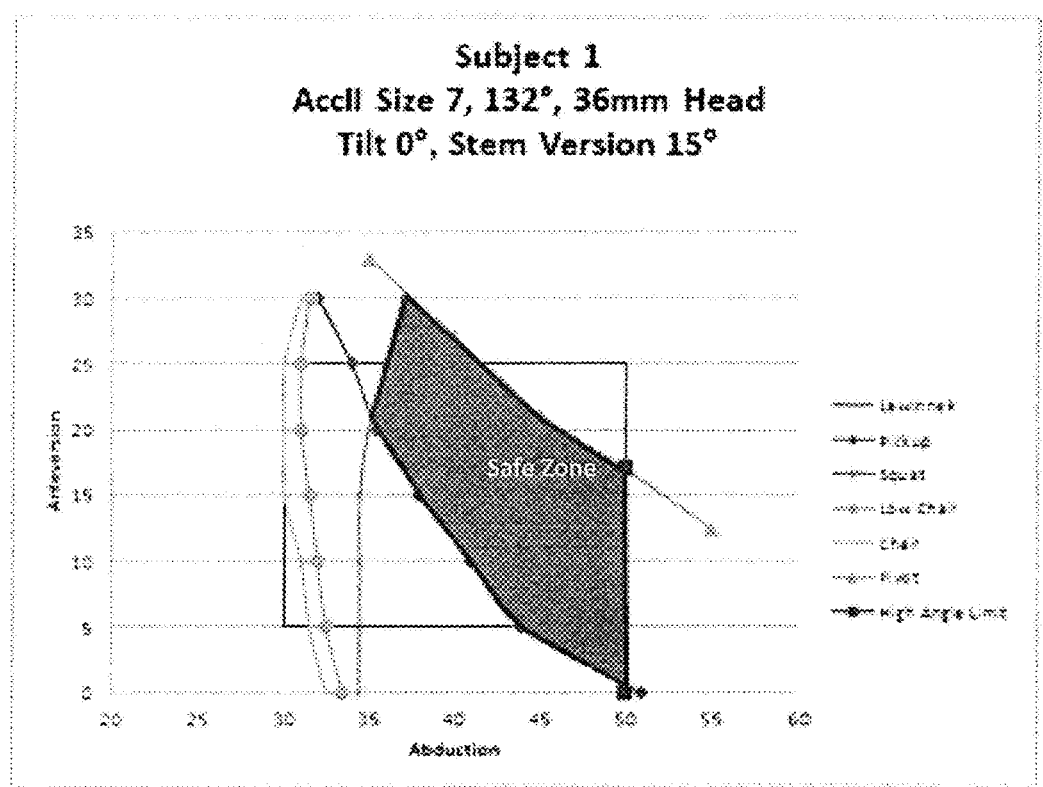
FIGS. 22-26 show safe zones for a size 7 hip implant for various pelvic tilts and stem versions.

FIG. 22 shows a safe zone for a size 7 hip stem (Accolade Stryker Corp) with 0° pelvic tilt and a stem version of 15° for subject 1.

Figure 23:
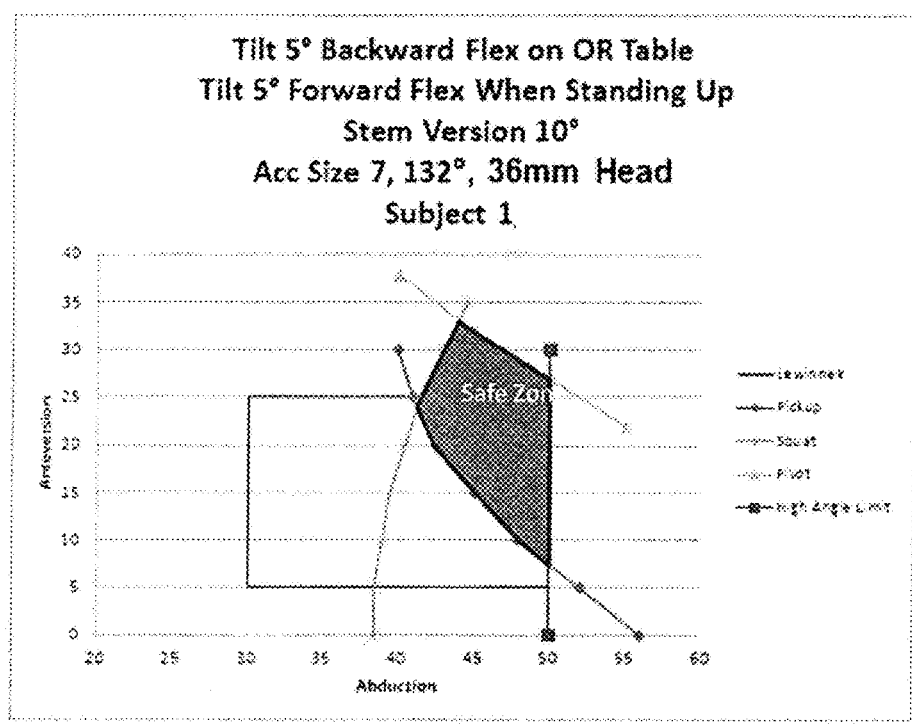

FIG. 23 shows a safe zone for a 5° forward pelvic tilt in standing x-ray and 5° backward pelvic tilt on OR table and stem version of 10° for subject 1.

Figure 24:
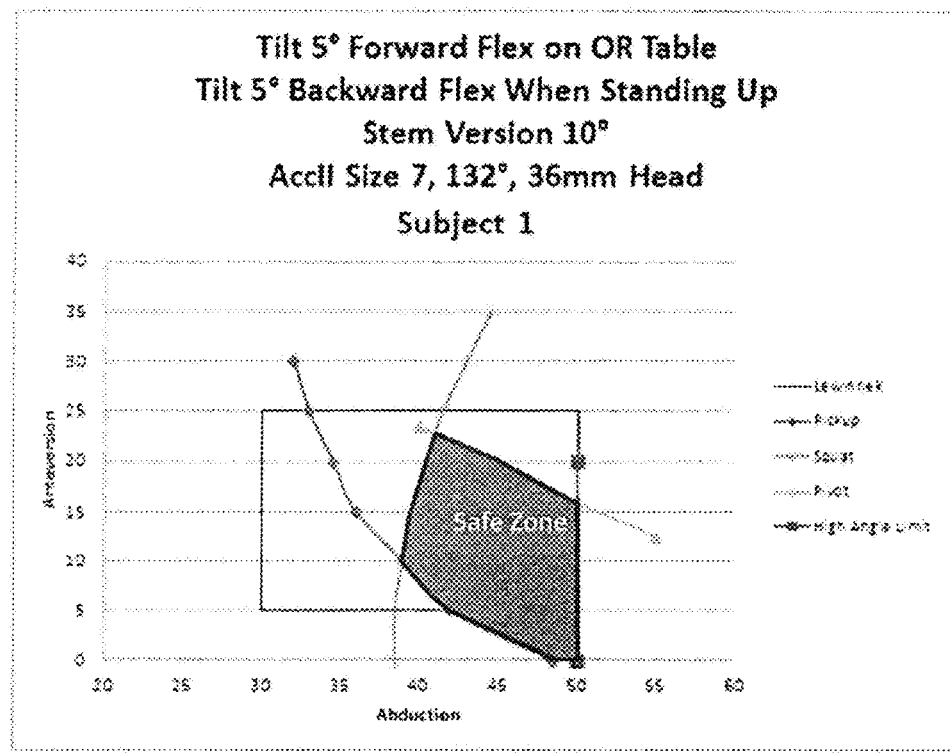

FIG. 24 shows a safe zone for a 5° backward pelvic tilt when standing x-ray is 5° forward pelvic tilt on OR table with 10° stem version for subject 1.

Figure 25:
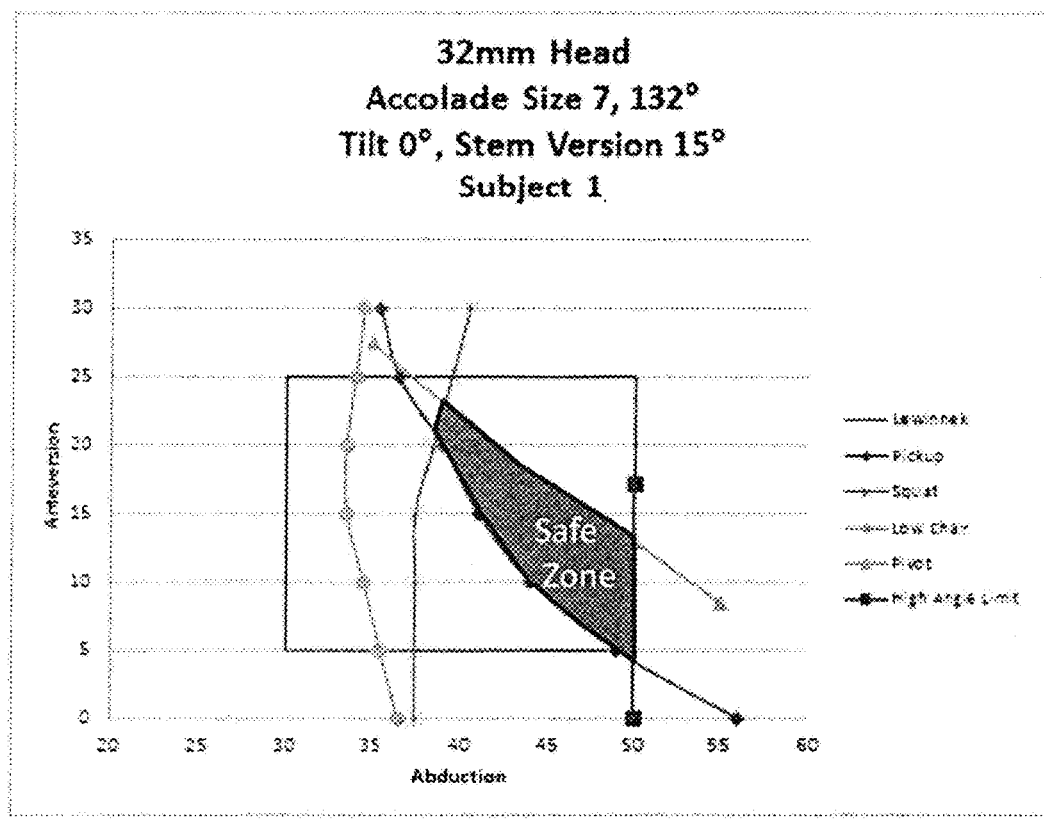

FIG. 25 shows a safe zone for 0° pelvic tilt and a stem in 15° version for subject 1.

Figure 26:
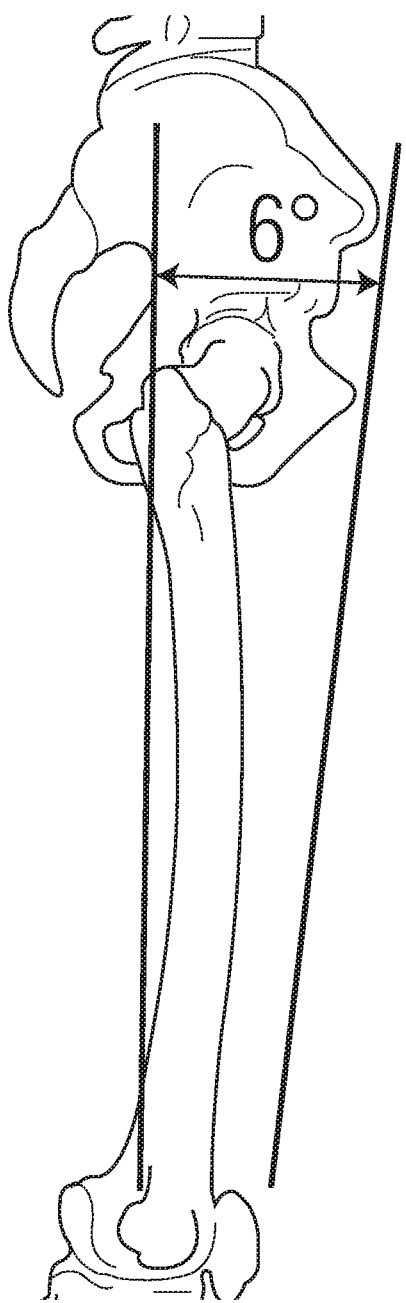

FIG. 26 is a standing lateral x-ray showing pelvic tilt shows a safe zone for 0° pelvic tilt and a stem in 15° version for subject 1.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for avoiding impingement between an implanted prosthetic femoral component and acetabular cup, comprising:

obtaining a lateral x-ray of a standing patient;
determining a pelvic tilt angle of the patient from the standing x-ray;
virtually implanting a hip stem at an initial femoral component version angle into a virtual femur;
obtaining data of at least one hip joint motion from at least one individual;
calculating a range of inclination and anteversion angles for a virtually implanted acetabular cup that avoids impingement with the virtually implanted femoral component; and
wherein the calculated range of inclination or anteversion angles is based at least in part on the pelvic tilt angle of the patient, the initial hip stem version angle and the obtained joint motion data,
wherein the pelvic tilt angle is a pelvic flexion angle of the standing patient,
wherein a safe zone is calculated when calculating the range of inclination and anteversion angles for the virtually implanted acetabular cup, the safe zone being where impingement with the virtually implanted femoral component at the initial version angle is avoided throughout a range of one hip joint motion, the safe zone being determined based on the determined pelvic tilt angle of the patient and at least one curve plot of the at least one hip joint motion.

2. The method as set forth in claim 1, wherein the hip motion data is selected from the group consisting of pivoting on one foot, rolling over in bed, getting in and out of a car, squatting, sitting in a chair, rising from a chair, picking up an object, climbing up stairs, climbing down stairs, rising from a toilet and walking.

3. The method as set forth in claim 1, wherein the virtually implanted acetabular cup is virtually implanted at multiple inclination angles and multiple anteversion angles.

4. The method as set forth in claim 1, wherein the digitized hip joint motion data is obtained from external motion detecting elements mounted on the at least one individual.

5. The method as set forth in claim 1, wherein the obtained hip motion data includes flexion-extension angles, internal-external rotation and adduction-abduction angles of the femoral component with respect to the virtual femur.

6. The method as set forth in claim 1, wherein the virtual hip stem and acetabular cup are selected from a group of commercially available hip stems and acetabular cups.

7. A method for avoiding impingement between an implanted prosthetic hip stem and acetabular cup, comprising:

obtaining an x-ray of a standing patient;
determining a pelvic tilt angle of the patient from the standing x-ray;
virtually implanting a hip stem at an initial stem version angle into a virtual femur;
obtaining hip joint motion data from at least one individual moving through one or more typical human activities; and
calculating multiple acetabular cup inclination and version angles of a virtually implanted acetabular cup that avoids impingement between the virtual hip stem implanted at the initial stem version angle while utilizing the hip joint motion data of the at least one individual based on the patient pelvic tilt angle,
wherein the pelvic tilt angle is a pelvic flexion angle of the standing patient,
wherein a safe zone is calculated when calculating the range of inclination and anteversion angles for the virtually implanted acetabular cup, the safe zone being where impingement with the virtually implanted hip stem at the initial stem version angle is avoided throughout a range of hip joint motion of the one or more typical daily human activities, the safe zone being determined based on the determined pelvic tilt angle of the patient and at least one curve plot of the at least one hip joint motion.

8. The method as set forth in claim 7, wherein the at least one individual is a patient receiving the prosthetic hip stem and acetabular cup.

9. The method as set forth in claim 8, wherein the hip joint motion data is from an average of at least two or more individuals.

10. The method as set forth in claim 8, wherein the hip join motion data from individuals are categorized according to variables such as gender, age, pre-operative motion abilities, previous operations, arthritic conditions, comorbidities, intended post-operative motion goals.

11. The method as set forth in claim 10 wherein the categorized motion data is used to determine the safe zone for patients with similar characteristics.

12. The method as set forth in claim 8, wherein the typical daily activities are selected from at least one group consisting of pivoting on one foot, rolling over in bed, getting in and out of a car, squatting, sitting down in a chair, rising from a chair, picking up an object, climbing up stairs, climbing down stairs, sitting on a toilet, rising from a toilet and walking.

13. The method as set forth in claim 10 wherein the motion data comprises data from at least 50% of the total motion of each activity.

14. The method as set forth in claim 8, wherein the virtual hip stem and acetabular cup are selected from a group of commercially available hip stems and acetabular cups.

15. The method as set forth in claim 8, wherein data for virtual representation of the hip stem and acetabular cup are obtained from a computer aided design (CAD) system used for the fabrication of the hip stem and acetabular cup.

* * * * *